(12) United States Patent
Takeda

(10) Patent No.: US 8,951,474 B2
(45) Date of Patent: Feb. 10, 2015

(54) DISPOSABLE CHIP-TYPE FLOW CELL AND FLOW CYTOMETER USING SAME

(75) Inventor: Kazuo Takeda, Mitaka (JP)

(73) Assignee: On-Chip Biotechnologies Co., Ltd., Tokyo (JP)

( * ) Notice: Subject to any disclaimer, the term of this patent is extended or adjusted under 35 U.S.C. 154(b) by 372 days.

(21) Appl. No.: 13/148,271

(22) PCT Filed: Feb. 5, 2010

(86) PCT No.: PCT/JP2010/051694
§ 371 (c)(1),
(2), (4) Date: Aug. 18, 2011

(87) PCT Pub. No.: WO2010/090279
PCT Pub. Date: Aug. 12, 2010

(65) Prior Publication Data
US 2011/0294139 A1 Dec. 1, 2011

(30) Foreign Application Priority Data
Feb. 6, 2009 (JP) ................. 2009-026794

(51) Int. Cl.
*B01L 3/00* (2006.01)
*G01N 21/64* (2006.01)
(Continued)

(52) U.S. Cl.
CPC ........ *G01N 15/1484* (2013.01); *G01N 15/1427* (2013.01); *G01N 15/1459* (2013.01); *G01N 2015/149* (2013.01)
USPC ........ 422/82.08; 422/402; 422/403; 422/417; 422/68.1; 422/73; 422/82.11; 422/502; 422/554; 435/286.5; 435/286.6; 435/288.7; 436/518; 436/523; 436/10; 436/171; 436/172

(58) Field of Classification Search
USPC .............. 422/402, 403, 417, 68.1, 73, 82.08, 422/82.11, 502, 554; 435/286.5, 286.6, 435/288.7; 436/518, 523, 10, 171, 172
See application file for complete search history.

(56) References Cited

U.S. PATENT DOCUMENTS

| 3,710,933 A | 1/1973 | Fulwyler et al. |
| 3,826,364 A | 7/1974 | Bonner et al. |

(Continued)

FOREIGN PATENT DOCUMENTS

| JP | 63-1952 A | 1/1988 |
| JP | 64-3541 A | 1/1989 |

(Continued)

OTHER PUBLICATIONS

International Search Report for PCT/JP2010/051694 dated May 11, 2010.
(Continued)

*Primary Examiner* — Gail R Gabel
(74) *Attorney, Agent, or Firm* — Heslin Rothenberg Farley & Mesiti PC

(57) ABSTRACT

The present invention provides an apparatus for analyzing particles in a solution including a unit configured to place a flow cell having a flow path for flowing a sample solution containing the particles; a unit configured to illuminate the sample solution flowing through the flow path of the flow cell; a photodetector that detects a scattered light and/or fluorescence generated from the particles in the sample solution; and a unit configured to analyze the particles based on their signal intensities detected by the photodetector, wherein the flow cell has the flow path formed in a substrate, a reflection plane is formed on the side surface of the flow path, the reflection plane leads the lights generated in the flow path of the flow cell and advancing in the substrate in-plane direction to a specified region of the surface of the flow cell, and the photodetector detects the light exiting from the specified region to the outside.

3 Claims, 14 Drawing Sheets

(51) Int. Cl.
*G01N 21/00* (2006.01)
*G01N 15/14* (2006.01)

(56) References Cited

U.S. PATENT DOCUMENTS

| | | | |
|---|---|---|---|
| 4,756,427 A | 7/1988 | Göhde et al. | |
| 6,454,945 B1 * | 9/2002 | Weigl et al. | 210/634 |
| 6,808,075 B2 | 10/2004 | Böhm et al. | |
| 7,105,355 B2 * | 9/2006 | Kurabayashi et al. | 436/165 |
| 2003/0054558 A1 | 3/2003 | Kurabayashi et al. | |

FOREIGN PATENT DOCUMENTS

| | | |
|---|---|---|
| JP | 1-170853 A | 7/1989 |
| JP | 3-150446 A | 6/1991 |
| JP | 4-55740 A | 2/1992 |
| JP | 9-218149 A | 8/1997 |
| JP | 2003-302330 A | 10/2003 |
| JP | 2004-77305 A | 3/2004 |
| JP | 2005-91093 A | 4/2005 |
| JP | 2005-91169 A | 4/2005 |
| JP | 2007-56094 A | 3/2007 |
| WO | 96/28732 A1 | 9/1996 |
| WO | 98/10267 A1 | 3/1998 |
| WO | 2004/101731 A1 | 11/2004 |
| WO | 2006/076195 A2 | 7/2006 |

OTHER PUBLICATIONS

Hoshino A., et al., "Separation of Murine Neutrophils and Macrophages by Thermoresponsive Magnetic Nanoparticles" Biotechnology Progress, 2007, 23, pp. 1513-1516.

* cited by examiner

DISPOSABLE CHIP-TYPE FLOW CELL AND FLOW CYTOMETER USING SAME

CROSS REFERENCE TO RELATED APPLICATIONS

This application is a national stage filing under section 371 of International Application No. PCT/JP2010/051694 filed on Feb. 5, 2010, and published in Japanese on Aug. 12, 2010 as WO 2010/090279 and claims priority of Japanese application no. 2009-026794 filed on Feb. 6, 2009, the entire disclosure of these applications being hereby incorporated herein by reference.

FIELD OF THE INVENTION

The present invention relates to an apparatus having a function to analyze biological particles typical of a flow cytometer or a function to separate biological particles typical of a cell sorter, a measurement method realizing a novel function using the same, and a disposable flow cell chip.

RELATED ART

Flow cytometers are typically used for identifying various types of cells and biological fluids. Flow cytometers of the related art have an optically transparent flow cell made of quartz and formed with a flow path through which the cells to be individually identified flows. The flow of cells passing through the flow path concentratively flows to the center portion of the flow path by a sheath solution concentrically surrounding the flow of cells. The center portion of the flow path is illuminated with a laser beam. When a cell passes through an illumination region, light scattering depending on the size, shape, and refractive index of the cell occurs. To detect a cell specifically dyed with a fluorescent dye by fluorescence, the wavelength of the laser beam is determined in accordance with the type of the fluorescent dye. In this manner, the fluorescence as well as the scattered light for each of the cells is detected by a plurality of photodetectors based on the wavelength, enabling the diversifiable analysis of the cell. Technique of a flow cytometer is described in U.S. Pat. No. 3,710,933 (Patent Document 1). The flat-plate flow cell is described in Japanese Patent Application Laid-Open (JP-A) No. 2003-302330 (Patent Document 13) and U.S. Pat. No. 7,105,355 (Patent Document 14). As an illumination method of a flow cytometer, a method of measuring a precise signal light intensity by scanning the inside of a flow path with a laser beam is described in JP-A No. 63-1952, JP-A No. 3-150446, and JP-A No. 4-55740.

Existing cell sorting methods will now be described. A method described in U.S. Pat. No. 3,710,933 (Patent Document 1) or U.S. Pat. No. 3,826,364 (Patent Document 5) is a separation method currently adopted for common products. The method includes discharging droplets of a sample solution from a nozzle for droplet formation into air, and separating each of the droplets including cells to be separated by an electric field. Japanese Patent Application Laid-Open (JP-A) No. 64-3541 (Patent Document 6) discloses a method that includes steps of flowing a sheath flow to periphery of a sample solution flowing through a flow cell, and shifting charged particles from a sample flow to the sheath flow by applying an electric field to the sample solution for separation and measurement. Japanese Patent Application Laid-Open (JP-A) No. 1-170853 (Patent Document 7) describes a method that includes steps of applying a pressure pulse to a particle flowing through a flow cell, and separating the particles into a flow path which is different from a flow path for steady flow in the flow cell. International Publication No. WO98/10267 (Patent Document 8) discloses a technique that includes applying a field to a flow of microparticles, the flow of which was narrowed by a sheath flow in the flow cell, and shifting the flow of the microparticles for separation. International Publication No. WO2004/101731 (Patent Document 9) discloses a method of separating a cell charged in a solution by gel electrodes disposed on both sides of a flow path in a flow cell by an electric field. U.S. Pat. No. 6,808,075 (Patent Document 10) discloses a method that includes steps of applying a pressure pulse by a babble valve forming a meniscus perpendicularly with respect to the flow of particles, and shifting the flow for separation. WO2006/076195 (Patent Document 11) discloses a method that includes a step of applying a pressure pulse as in International Publication No. WO98/10267, but also includes steps of ejecting each droplet including target particle, and collecting it into a container. U.S. Pat. No. 4,756,427 (Patent Document 12) describes a method that includes steps of measuring each particle in a flow of a sample solution narrowed by a sheath flow, and if it is judged that the particle is a target particle, introducing the particles into a different flow path by a pulse flow for separation. A method that includes using magnetic particles coated with an antibody, absorbing the magnetic particles to a particular cell, and separating it by a gradient magnetic field is known (International Publication No. WO96/28732). A thermo-responsive magnetic nanoparticle which can be coagulation-controlled by temperature is disclosed (JP-A No. 2007-56094). A method of separating a cell using a thermo-responsive magnetic nanoparticle is disclosed (Hoshino A, et al. Biotechnology Progress, 2007, 23, 1513-1516).

SUMMARY OF THE INVENTION

There is a biohazard problem in relation to a conventional flow cytometer and a cell sorter. This is because an inclusion of an outside foreign substance into a measurement sample and a spread of the measurement sample to outside occur. In other words, it is impossible for a conventional flow cytometer to readily change the solution sending system including a sample solution reservoir, a solution sending pipe, and a flow cell. Therefore, to prevent carry-over, a flow cytometer is needed to be cleaned for each measurement of different samples. This is ditto for a cell sorter which is a flow cytometer with an additional function of separation of microparticles. A solution to this is to make the flow cell disposable. To make a flow cell disposable, it is preferable that the flow cell has a flat-plate configuration like a glass slide. This is because a flat-plate flow cell enables mass production of flow path patterns easily and inexpensively by injection molding. When a flat-plate flow cell is used, it is preferable to emit an illumination laser perpendicular with respect to the surface of the flow cell. However, there is a problem in detection of a scattered light in an in-plane direction of the substrate; that is, a sideward scattered light. The flow cell of the general flow cytometer typically has a square cross section, whereby a scattered light perpendicular to the laser illumination direction is measured without any problems together with a forward scattered light at the same time. However, when a flat-plate flow cell is used, the substrate of the flow cell exists in the direction of a sideward scattered light. Consequently, the flat-plate configuration of a flow cell results in an obstacle to measurement. As a method of solving this problem, U.S. Pat. No. 7,105,355 describes a method that includes disposing an optical fiber on the side surface of a flow path of a flow cell, and leading a light generated in the flow path to a photodetector. However, in this case, the optical fiber is connected to the flow cell, making the flow cell unsuitable for replacement for each measurement. Thus, this method is not applicable to the disposable flow cell.

In addition, it is difficult to make the flow cell disposable unless it is manufactured at low cost. The flow cell is preferably made of a transparent resin in order to manufacture it inexpensively. However, the resin slightly has a light absorption band in the region of a short wavelength below 500 nm and generates fluorescence, resulting in background noise of measurement. In other words, in the case of a flow cell made of a transparent resin which is suitable for making it disposable, the self-fluorescence is an obstacle to measurement.

A problem in relation to a microparticle separation method will now be discussed. A first problem is a biohazard problem. The droplet discharge method by a jet nozzle described in U.S. Pat. Nos. 3,710,933 or 3,826,364 has the biohazard problem. In other words, when a sample is a cell contaminated with pathogenic virus or bacteria, the method has a risk of spreading a very dangerous substance as an aerosol into the atmosphere. As a method for solving the first problem, a method of separating the cell by confining the aerosol in the flow cell without spreading them into the atmosphere can be considered. Some of these techniques have been published. JP-A No. 64-3541 discloses a method that includes steps of flowing a sheath flow around a sample solution flowing in a flow cell, and shifting charged particles in the sample solution from a sample flow to the sheath flow by applying an electric field to the sample solution for separation and measurement. JP-A No. 1-170853 discloses a method that includes applying a pressure pulse to a particle flowing through a flow cell, and separating the particle into a flow path which is different from a flow path for steady flow in the flow cell. There is a problem for this method in that it has a cumbersome process to avoid the separated particle from returning to the original flow path. International Publication No. WO98/10267 discloses a technique that includes applying an electric field or a magnetic field to particles flowing in a narrow flow which is surrounded by a sheath flow in a flow cell, and shifting the flow of the particles for separation. If an electric field is used as the field in this method, it corresponds to the method of JP-A No. 64-3541. A method that utilizes an electric field in the same way as that disclosed in International Publication No. WO2004/101731 is not suitable for practical use in sorting with electrolytes because the method has a problem in that even if an occurrence of babbles by electrolysis is prevented by some means, an electric charge of a cell is shielded by ions contained in electrolytes surrounding the cell, resulting in the lowering of the force acting on the particles. U.S. Pat. No. 6,808,075 discloses a technique of sorting with a chip. A reciprocating motion of a meniscus is required for separating a particle, and flows of an advance direction and a return direction are opposite. Consequently, the meniscus is required to return to the original position after the particle is moved away sufficiently. International Publication No. WO2006/076195 discloses a method that includes applying a pressure pulse as in JP-A No. 1-170853, ejecting each droplet in a region including a target cell, and collecting it into a container. This cannot be realized in a disposable flow cell chip and has a problem of contamination with other samples. In U.S. Pat. No. 4,756,427, the technique is not directly applicable to the disposable chip.

A second problem will be described. Let us assume that the density of non-target cells is much higher by, for example, 100 times or above than that of target cells for sorting. The highest separation performance at present is about 95%. A problem arises that separated cells include more non-target cells than target cells.

Therefore, to increase the purity of the separated cells, the collected samples are required to be subjected to a sorting process again. However, since an absolute number of target cells is small, repetition of this process increases the probability that the target cells can be lost. In most cases, repeating a separation cannot be a solution.

There will be described problems of a method that includes using magnetic particles coated with a particular antibody, absorbing the magnetic particles to a cell having an antigen to the antibody, and separating the cell by a gradient magnetic field. One of the problems is that since the separation accuracy is determined only by the specificity of one antigen-antibody reaction, it is difficult to improve the separation accuracy using a large number of antigen-antibody reactions. In other words, it is difficult to separate a cell labeled by magnetic particles coated with an antibody by a gradient magnetic field and to separate a particular cell by magnetic particles coated with another antibody from the separated cell. This is because the plurality of magnetic particles cannot be selectively separated and it is difficult to remove the magnetic particles from the separated cell. In any case, for the conventional method of separating a cell using magnetic particles, the specificity of one antigen-antibody reaction determines the limit of the separation accuracy. A second problem is that it is not certain that a cell separated by magnetic particles is truly separated. The separated cell is required to be analyzed by a flow cytometer for identification. However, since a typical flow cytometer uses a sheath solution in large quantity, the measured cell fluids are diluted at least about 1000 times. When the number of cells is very small, a risk of losing the cells is high.

The present invention has been made in view of the above circumstances and provides the following: an apparatus which uses a disposable flow cell to analyze and identify a biological particle, an apparatus for separating it, and the disposable flow cell.

(1) An apparatus for analyzing particles in a solution including:

a unit configured to place a flow cell having a flow path for flowing a sample solution containing the particles;

a unit configured to illuminate the sample solution flowing through the flow path of the flow cell;

one or more photodetectors that detects, based on the wavelength, scattered light and/or fluorescence generated from a particle in the sample solution; and a unit configured to analyze the particles based on their signal intensities detected by the one or more photodetectors, wherein the flow cell has the flow path formed in a plate substrate, a reflection plane is formed on the outer side surface of the flow path, the reflection plane directs the light which is generated in the flow path of the flow cell and advancing in the substrate in-plane direction to a specified region of the surface of the flow cell, and the photodetector detects the light exiting from the specified region to the outside.

(2) The apparatus for analyzing particles in a solution according to item (1), wherein the reflection plane formed on the outer side surface of the flow path is a plane formed from the interface between the side surface of the flow path and an atmospheric gas, and is a plane that totally reflects the light arriving from the flow path.

(3) The apparatus for analyzing particles in a solution according to item (1), wherein the flow cell is flat-plate and has a configuration that allows an illumination light to enter into the flow path substantially perpendicularly to the surface of the substrate of the flat-plate flow cell; sideward scattered light generated in the flow path and traveling sideward of the flow path is detected as the light is directed from the specified region of the flow cell to outside making use of the reflection surface integrated in the substrate of the flow cell; and a forward scattered light is detected as the light passes through the flow cell forward to exit to the outside.

(4) A flow cell for detecting light generated from a sample particle in a sample solution which is illuminated with light while the sample solution flows through a flow path in the flow cell, wherein a reflection plane is formed which gives total reflection of the light advancing from the direction of the flow path to the outside of the side surface of the flow path in the flow cell, and the reflection plane is a reflection plane formed from an interface between the basic material of the flow cell and an atmospheric gas.

(5) The flow cell according to item (4), wherein the flow cell has a flow path formed in a transparent plate substrate, and the reflection plane reflects scattered light and fluorescence generated within the flow path toward the top surface or the bottom surface of the substrate.

(6) The flow cell according to item (4), wherein the flow cell has a flow path formed in a transparent plate substrate, and the reflection plane functions as a reflection plane for reflecting an illumination light incident on the flow cell, and illuminating the flow path from an in-plane direction of the substrate.

(7) A flow cell for detecting light generated by a sample particle in a sample solution which has been illuminated with light while the sample solution flows through a flow path in the flow cell, wherein the flow cell has a flow path formed in a transparent plate substrate, and the light reflection plane in the substrate of the flow cell is an interface between the top flat surface or the bottom flat surface of the plate substrate and an atmospheric gas, or a side surface of a groove configuration formed in the top or bottom surface of the substrate, and directs light which is generated in the flow path and advances within the plate substrate in an in-plane direction to the specified outside surface of the flow cell.

(8) The flow cell according to item (7), wherein the light reflection plane is formed as an inclined surface at about 45° to the surface of the substrate beside the flow path, and reflects the light which is generated in the flow path and advances within the substrate in an in-plane direction toward the top surface or the bottom surface of the substrate.

(9) The flow cell according to item (7), wherein the thickness of a specified local region including the flow path in the flow cell to be illuminated is smaller than that of the periphery region thereof.

(10) The flow cell according to item (7), wherein the flow cell has a flow path, and reservoirs on an upstream side and a downstream side of the flow path on the substrate, and the solution flowing through the flow cell is confined in the system consisting of the upstream reservoir, the flow path, and the downstream reservoir.

(11) An apparatus for measuring a particle in a solution including:

a unit configured to place a flow cell having a flow path for flowing a sample solution containing a sample particle;

a unit configured to illuminate the sample solution flowing through the flow path of the flow cell;

one or more photodetectors that detects scattered light or fluorescence generated from the sample particle in the sample solution; and a unit configured to identify the sample particle based on their signal intensities detected by the one or more photodetectors, wherein the flow cell has an array of a plurality of flow paths in a plate substrate in an in-plane direction, the illumination unit illuminates the flow paths with an illumination beam in the direction in which the light crosses the flow paths, and the photodetector distinguishes and measures the light signals generated from the sample particles flowing through the flow paths.

(12) An apparatus for measuring particles in a solution including:

a unit configured to place a flow cell having a flow path for flowing a sample solution containing a sample particle;

a unit configured to illuminate the sample solution flowing through the flow path of the flow cell;

one or more photodetectors that detects a scattered light or fluorescence generated from the sample particle in the sample solution based on the wavelength; and a unit configured to identify the sample particle based on its signal intensity detected by the one or more photodetectors, wherein the flow cell has an array of a plurality of flow paths, the illumination unit has a mechanism enabling relative scanning of the flow paths with an illumination beam in the direction in which the light crosses the flow paths, the beam size is smaller than the width of each of the flow paths, the scanning period is larger than the response frequency of the light detection signal, and a detection optical system of the photodetector is an image formation optical system and has an array type detector disposed on an image formation plane of the flow paths so as to distinguish the flow paths for simultaneous parallel measurement.

(13) A flow cytometer and a flow cell thereof for detecting the light generated by a sample particle in a sample solution which has been illuminated with light while the sample solution flows through a flow path in the flow cell, wherein the flow cell is plate and comprises: a plurality of sample solution reservoirs and a sheath solution reservoir which is common to a plurality of sample solutions and is formed on a plate substrate, wherein the sample solution reservoirs are formed in the common reservoir so as not to mix the solutions; a flow path for sample solution which is connected to each of the sample solution reservoirs; and flow paths joining sheath flows from the left and right sides of the sample solution flows, the joining flow paths are formed so as to be parallel at equally spaced intervals, the most downstream is connected to a common reservoir formed on the flow cell, and the illumination beam of a size illuminating only one of the flow paths or the flow cell is sequentially moved by a step and repeat system to measure a plurality of samples.

(14) The apparatus for measuring particles in a solution according to item (12), wherein the flow cell has an array of a plurality of capillaries.

(15) An apparatus for separating particles, comprising: illuminating a sample solution which contains biological particles while the sample solution flows through a flow path in a flow cell; detecting scattered light and fluorescence generated from the particle; and identifying and separating particles based on its signal intensity, and wherein the flow cell comprises:

the flow path formed in a plate substrate;

a flow path to introduce a sample solution;

a pair of flow paths to introduce a sheath solution arranged on both sides of the flow path to introduce the sample solution;

a joining flow path joining these and flowing a sheath solution on both sides of the sample solution; and a flow path S is connected to at least one side surface of the joining flow path to the downstream side of a illumination region, wherein it is judged whether or not the particle is to be separated by the light signal generated when the particle pass through the illumination region, if it is judged that the particle is to be separated, a pulse flow is applied from a pump disposed outside the flow cell to the particles flowing through the flow path S into the joining flow path while the particles pass through the portion connected to the flow path S so as to shift the flowing position of the particle in the joining flow path, if it is judged that the particle is not to be separated, the pulse flow is not generated so that the flowing position is not shifted, and the particle is separated into each of a plurality of branched flow paths on the downstream according to the presence or absence of the shift.

(16) An apparatus for separating particles comprising:

a unit configured to place a flow cell comprising a flow path for flowing a sample solution containing particles;

a unit configured to illuminate the sample solution flowing through the flow path of the flow cell;

one or more photodetectors that detects, based on the wavelength, a scattered light and/or fluorescence generated from a particle in the sample solution; and a unit configured to identify and separating the biological particle based on a plurality of signal intensities detected by the one or more photodetectors, wherein the flow cell comprises:

a flow path for introduction of a sample solution;

a pair of flow paths for introduction of a sheath solution arranged on both sides of the flow path for introduction of the sample solution;

a joining flow path that joins aforementioned flow paths and allows the sheath solution and the sample solution to flow with the sheath solution being on both sides of the sample solution; and a flow path S which is connected to at least one side surface of the joining flow path downstream of an illumination region, wherein a light signal generated from a particle when the particle passes through the illumination region is detected so as to judge whether or not the particle is to be separated, if it is judged to be separated, a negative pressure pulse is applied from a pulse pump via a reservoir on the flow cell connected to the downstream side of the flow path S and atmospheric gas in a sealed space to the particle flowing through the flow path S into the joining flow path while the particle passes through a location of the joining flow path connected to the flow path S so as to fetch the particle into the flow path S for storing the particle in the reservoir, and the particle is separated while an entire solution sending system is confined to one flow cell.

(17) An apparatus for separating particles in a solution including:

a unit configured to place a flow cell having a flow path for flowing a sample solution containing the particles;

a unit configured to illuminate the sample solution flowing through the flow path of the flow cell;

one or more photodetectors that detects, based on the wavelength, a scattered light and/or fluorescence generated from a particle in the sample solution; and a unit configured to identify and separate the particles based on a plurality of signal intensities detected by the one or more photodetectors, wherein said flow cell comprises:

a flow path into which a sample flow and a sheath flow join, and in which the sample solution flows while being cross-sectionally eccentrically localized in the flow path;

an electromagnet which is disposed beside the flow path, and can control application of a magnetic field to a narrow joint flow of the sample flow and the sheath flow;

a branched flow path 1 into which only a magnetized particle is shifted and introduced from the sample flow, wherein the magnetized particle is subjected to a laser beam irradiation, and determined as to whether the magnetized particle is of interest;

a flow path S which is connected to and formed downstream of the branched flow path 1;

a reservoir S connected to the downstream side of the flow path S; and a pulse pump, wherein if the magnetized particle is found to be of interest, the particle is flowed into the flow path S, and is fetched into the reservoir S by an attraction force pulse flow generated by the pulse pump and the reservoir S which is air sealed.

(18) A flat-plate flow cell for separating particles contained in a sample solution while the sample solution flows through a flow path, including:

a transparent substrate on which a flow path is formed, and on which reservoirs are formed at the upstream side and the downstream side of the flow path;

a flow path for introduction of a sample solution;

a pair of flow paths for introduction of a sheath solution, arranged along both sides of the flow path for introduction of the sample solution; and a joining flow path for joining these, in which the sheath solution flows along both sides of the sample solution;

a flow path S which is connected to at least one side surface of the joining flow path, wherein the flow path S has a port which can be pipe connected to the outside; and a plurality of branched flow paths for separation, which are formed on a downstream side of the joining flow path and are connected to the reservoirs.

(19) A flow cell for separating particles contained in a sample solution while the sample solution flows through a flow path, including:

a transparent substrate on which a flow path is formed, and reservoirs are formed at an upstream side and a downstream side of the flow path;

a flow path for introduction of a sample solution;

a pair of flow paths for introduction of a sheath solution, arranged along both sides of the flow path for introduction of the sample solution; and a joining flow path for joining these, in which the sheath solution flows along both sides of the sample solution;

a flow path S which is connected to at least one side surface of the joining flow path; and a reservoir for separated particle, which is connected downstream of the flow path S; wherein the reservoir has a port which can be pipe connected to the outside, and the joining flow path is connected to a discharged solution reservoir on the downstream side.

(20) A method of separating a particular cell from a large number of cell groups, including:

allowing different antibodies to react with a variety of cell groups based on antigen-antibody reactions, wherein a plurality of thermo-responsive magnetic particles in which the temperatures of coagulation and dispersion are bonded to the different antibodies;

separating a cell by a gradient magnetic field, wherein the separation is sequentially performed at a plurality of temperatures based on a plurality of antigen-antibody reactions so as to perform selection and separation.

(21) The apparatus for measuring particles in a solution according to any one of items (1), (2), (3), (11), (12), (13), (14), (15), (16), and (17), wherein measurement can be made by controlling the temperature of the sample solution.

The features of the present invention will be described below.

1) Unit that Detects a Sideward Scattering Signal Using a Disposable Flat-Plate Flow Cell In a flow cell for illuminating a sample solution while the sample solution flows through a flow path in the flow cell and detecting a light generated from a substance in the sample solution, a flow path pattern, through which the sample solution flows, and a light reflection plane 4 that leads the light generated in the flow path to the specified surface of the flow cell are formed. A total reflection plane is formed in the flow cell using an interface between the basic material of the flow cell and a gas. When the refractive index of the basic material of the flow cell is Nf and the refractive index of the atmosphere is 1, the critical incident angle is obtained by a sin (1/Nf). All the incident angles larger than this angle provide total reflection. For instance, when Nf=1.42, the angle is 44.7°. For the refractive index of specific materials in the wavelength range from 400 to 800 nm, Nf=1.45 to 1.47 for quartz, Nf=1.50 to 1.53 for glass, Nf=1.49 to 1.50 for acryl, and Nf=1.64 to 1.7 for polycarbonate. It is found that all of these materials satisfy the total reflection condition at an incident angle of 45° or above in the visible light region.

The reflection plane is formed in the flow cell so that the light generated in the flow path can be reflected on the specified surface of the flow cell at high efficiency and be led. As the refractive index of the basic material of the flow cell is higher, the critical incident angle is smaller so that the incident angle range satisfying the total reflection condition is increased. To efficiently lead the light, a basic material of the flow cell having a high refractive index is preferable. In the flow cell shown in FIG. 1, the planes of the front and rear surfaces of the flat-plate flow cell function as the total reflection planes. A signal light 6 (scattered light or fluorescence) generated the instant that a cell flowing through a flow path 5 passes through an illumination region 1 and advancing sideward (in the in-plane direction on the flat-plate substrate) generates total reflection on the front and rear surfaces 4 of the flow cell in the range of ±45°, which is efficient for detecting the light exiting to the outside of an end face.

In the configuration shown in FIG. 2, grooves 7 are formed in a flat-plate substrate of the flow cell. The side surfaces 4 at the boundary between a resin and a gas can also be a total reflection plane. As a result, the light generated from the inside of the flow path is efficiently led to the end face by the upper, lower, left, and right total reflection planes so that the sideward signal light can be efficiently detected in the direction of the end face in the flow cell. In the flow cell shown in FIGS. 3 and 4, an inclined surface is fabricated to form a total reflection plane for directing a sideward signal light in or at an end face of the substrate, and is used to reflect a signal light toward the front surface direction or the rear surface direction. In this way, it is made possible to exhibit total reflection in the flow cell used for the flow cytometer so that the sideward signal light can be detected by the flat-plate flow cell. The following means is adopted as the optical system for detection using the total reflection of the flow cell.

As shown in FIG. 1 or 2, when the flow path is illuminated perpendicularly with respect to the plane of the flat-plate flow cell to detect the sideward signal in the end face of the substrate, the signal light exiting from the end face to the outside is required to be efficiently detected. For this reason, a flexible light guide tube 17 is disposed near the end face to lead the light to a photodetector 2. This enables a free arrangement of the photodetector. Even if a relative position of the flow cell to the detection optical system is not strict, a signal light, which is incident upon the end face of the light guide, can be led to the photodetector at high efficiency.

In addition to the optical system for detection of the sideward signal light, an entire optical system of the flow cytometer using a disposable flow cell will be described.

As shown in FIG. 4, an illumination light 3 illuminates the flow path 5 substantially perpendicularly with respect to the substrate of the flow cell. For the detection of a scattered light and fluorescence generated from a sample particle, an optical system that includes a dichroic mirror 14 and a band pass filter 15 to separate and detect a signal light passing through the substrate of the flow cell and exiting the surface of the substrate based on wavelengths, and a detection system that includes a band pass filter 15 passing a signal light therethrough and a light guide 17 disposed outside the flow cell with the total reflection plane 4 formed in the flow cell for wavelength separation make it possible to lead the signal light to the detector 2 for detection, thereby enabling detection of a forward scattered light signal and a sideward scattered light signal having the same wavelength as that of the incident light, and fluorescence having a wavelength different from that of the incident light for each particle.

Unit that enables replacement of a solution sending system together with the flow cell and detection of the forward scattered light and the sideward scattered light is described as follows:

There is provided a biological-particle analyzing and separating apparatus which is an apparatus illuminating a sample solution containing a biological particle with an illumination light while the sample solution flows through a flow path in a flow cell, detecting a scattered light and fluorescence generated from the particle by the photodetectors, and identifying the particles based on their signal intensities, wherein as shown in FIG. 7, an upstream reservoir and a downstream reservoir connected respectively to the upper end and the lower end of the flow path of the flow cell are formed on the substrate of the flow cell; the flow rate of the sample solution flowing from the upstream reservoir to the downstream reservoir is controlled by applying a pressure to both the reservoirs via the air; the flow cell has the flow path formed in the flat-plate substrate; a sideward light, i.e., an in-plane light in the substrate, generated from a particle in the flow path, is led to a light guide disposed outside the flow cell using a total reflection plane fabricated on the substrate and is detected by the photodetector on the outside of the substrate as shown in FIG. 4; and a forward scattered light passing from the flow path through the substrate of the flow cell and exiting the front surface of the substrate is detected.

A flow cell incorporating the entire solution sending system and enabling reduced self-fluorescence sideward scattered light is configured as follows:

There is provided a flow cell flowing a sample solution containing particles, wherein the flow cell has a flow path formed in a transparent substrate and reservoirs formed in the upper portion of the substrate on the upstream side and the downstream side of the flow path, there are a flow path 1 for sample solution introduction connected to a sample reservoir on the upstream side, a pair of flow paths 2 for sheath solution introduction arranged on both side of the flow path for sample solution introduction 1 and connected to a sheath solution reservoir, and a flow path 3 joining these flow paths and flowing a sheath solution on both sides of the sample solution in laminar flow state, the thickness of the substrate in the region including part of the flow path 3 is smaller than the periphery thereof, as shown in FIG. 6, and a total reflection plane comprised of an interface between the surface of the substrate and the atmosphere and a total reflection plane comprised of an interface between an air layer formed in the substrate and the material of the substrate lead a scattered light generated in the flow path to a specified region at the end of the substrate.

Detection of the sideward scattered light is also enabled by using the total reflection plane for the illumination optical system. In other words, as shown in FIG. 5, when the total reflection plane 4 formed in the flow cell is used to illuminate the flow path 5 in an in-plane direction, the sideward signal light is detected by the detection optical system disposed under the substrate of the flow cell. The illumination system is effective as a unit configured to measure multiple specimens, which will be described next.

2) Unit that Realizes a Flow Cytometer for Multiple Specimens

As shown in FIG. 8, the method shown in FIG. 5 is applied to a flow cell with multiple flow paths. In this case, to distinctively detect signal lights such as scattered lights and fluorescence generated from the inside of the flow paths, the detection optical system adopts a method that includes forming an image of a flow path on an image formation plane 26 using an image formation lens and disposing an array detector 23 on the plane. The size of the detection plane is smaller than the width of each of the flow paths in the image formation plane. Measurement of signal pulses, which differ by each flow path, are performed in parallel for each of the flow paths in the flow cell. A light absorption member 25 prevents an intense reflection light of the illumination beam from returning to the flow path. FIG. 9 shows a method of illuminating multiple flow paths with the illumination light incident from an end face without using the total reflection plane in the flow cell. FIG. 10 is a top view of the flow cell of FIG. 8 formed with a plurality of flow paths and total reflection planes. When a side surface of the flow path is illuminated, a sheath solution is unnecessary so that a sheath solution reservoir is unnecessary. A pressurized gas reservoir 27 for applying the same pressure to a plurality of sample reservoirs is disposed.

FIG. 11 shows a method that detects a plurality of flow paths at the same time by scanning the flow paths at high speed with an illumination laser beam. For scanning at high speed, a deflector with an optical acoustic element is used. In this method, to distinctively measure the flow paths, an array detector is disposed on the image formation plane as the image formation system of the detection optical system as described above. The scanning period of the laser beam is higher than the time response frequency of the detector so that it is as if the scanning laser beam is one continuous beam of illumination for the detector. That is, it makes it possible for the measurement system to control the length of the line beam according to the scanning width. In this case, the frequency of the deflector with the optical acoustic element is 10 MHz or more and the responsive frequency of the photodetector is about several 10 KHz. When the scanning period of the laser beam is lower than the time response frequency of the detector, particles passing through the illumination region is illuminated plural times by the scanning beam so as to generate a plurality of signal pulses. This is disadvantageous because the signal processing is complicated. On the other hand, in the high-speed scanning mentioned above, one pulse signal is generated with respect to one particle.

FIG. 12 shows a method of sequentially measuring each of the plurality of flow paths by moving the flow cell or the laser beam by step and repeat. Since the detection optical system in this case is not required to distinguish the flow paths, the detector need not be an array detector. FIG. 13 shows a configuration of a flow cell adopted for the apparatus shown in FIG. 12. A sheath solution reservoir 9 is disposed such that the sheath solution is joined from the left and right sides of the sample flow paths and the flow of the sample solution is narrow enough to be smaller than the size of the illumination light beam. The particles in the sample solution sequentially stay for a fixed time in the center position of each of the flow paths formed at equally spaced intervals in the measurement region 1, then the laser beam is moved to the next flow path. Thus, the particles in the plurality of sample solutions are sequentially analyzed. Each of the flow paths is connected to a common discharged solution reservoir on the downstream side. The discharged solution reservoir is formed on the flow cell.

As shown in FIG. 14, the following means is configured to combine the flow cell having micro-capillaries integrated in an array format with an illumination system which makes use of high-speed scanning with a laser beam. It is intended that the advantage of this means is to automatically and sequentially measure the sample solution by directly absorbing it from a multi-well plate for sample pretreatment. A jig 35 for adjusting the capillary pitch is applied to adjust the array pitch of the sample solution of the multi-well plate. After completion of one measurement, the stage for a plate with multiple wells automatically displaces in longitudinal and lateral directions to suck a next sample solution array and perform measurements. FIG. 15 is a cross-sectional view of the capillary array type flow cell. Upon the illumination of the laser beam, the light is reflected at the boundary between different refractive indexes. A liquid having a refractive index of 1.42 same as that of quartz, which is a basic material of the capillary, is filled into a gap between the capillary arrays to reduce an occurrence of noise light.

4) Cell Sorter with a Disposable Flow Cell

A cell separation method using a flow cell shown in FIG. 16 will be described.

There is provided a method that includes illuminating a sample solution containing a biological particle with a laser beam while the sample solution flows through a flow path in a flow cell, detecting a scattered light and fluorescence generated from the biological particle, and identifying and separating the biological particle based on its signal intensity, wherein the flow cell has a flow path for sample solution introduction 45 connected to a sample solution reservoir 8 on the upstream side, a pair of flow paths for sheath solution introduction 46 connected to the sheath solution reservoir 9, and the flow path 5 joining these and flowing a sheath solution on both sides of the sample solution, a particle separation region 39 is located on the downstream side of a laser illumination region 1 where a flow path 47 is connected to the side surface of the flow path 5. A pair of the flow paths 47 are connected so as to correspond to each other. Pulse pumps are connected to respective flow paths 47. Up to two particles to be separated are identified by light signals generated when the particles pass through the laser illumination region 1. As shown in FIG. 17, when the particles flowing in the flow path 5 pass through the flow path 47 and the particles are those that are to be separated, pulse flows from the pulse pump, which is equipped two different separation modes, are applied to shift the flowing positions of the particles in the flow path 5. Based on the shift, the particles are separated into the branched flow paths on the downstream side of the flow path 5, in which the branched flow paths are branched depending on the timing when the two pulse pumps are off, when the right pulse pump is on, and when the left pulse pump is on. The principle of the separations is as follows: Three branched flow paths are formed on the most downstream part of the flow path 1 so as to be in substantially symmetrical configuration to the joining portion on the upstream side of the flow path 1 so that the sample solution and the sheath solution are divided again into the three branched flow paths and are collected. The particles typically flow into a middle flow path 44. The particles flows into a flow path 42 when they are shifted by the pulse flow of a pushing-out direction. The particles flows into a flow path 43 when they are shifted by the pulse flow in a reverse direction. As the pulse pump, a piezoelectric pump is suitable. The amount of one pulse flow can be controlled by a voltage provided to the piezoelectric pump.

The configuration of the flow cell for the cell separation method needs to satisfy the following requirements.

The flow cell has flow path 45 for introduction of a sample solution connected to sample solution reservoir 8, a pair of flow paths 46 for introduction of a sheath solution connected to sheath solution reservoir 9, and flow path 1 joining these and flowing a sheath solution on both sides of the sample solution. Flow path 47 is connected to a side surface of the flow path 1 on the downstream side of a laser illumination region. Three branched flow paths are formed on the most downstream side of the flow path 1 so as to be in substantially symmetrical to the joining portion on the upstream side of the flow path 1. The flow path 47 has a port connected to the outside of the flow cell. FIG. 19 shows a means in which there are only one flow path 47 and one pulse pump. In this case, only one kind of particles can be separated. In FIG. 17, a supplied solution tank for sorting is connected to a pulse pump because the pulse flow by the pulse pump is in the pushing-out direction. In the case of the pulse flow in the drawing-in direction, however, a collected solution tank for sorting is required. When the amount of drawing-in by the pulse flow is large, even the separated particles are drawn into the tank. To prevent this, the pulse flow rate is required to be adjusted. Considering biohazard, when a cell infected with virus is separated, it is desirable that the sample solution is confined in the flow cell, and the pulse flow is in the pushing-out direction. It can be said that the principle of the particle separation is to shift the flow of the particles by the pulse flow, and separate the particles into the branched flow path on the downstream side.

A method in which the shift of the flow of the particles is not used will be described with reference to FIGS. 18 and 19. A cell passes through a measurement region 1. It is judged whether or not the cell is to be separated based on an analysis of signal light in real time. If the cell is to be separated, the instant that the cell reaches region 39 near branch flow paths, a negative pressure pulse is generated by the pulse pump connected to the downstream side of a flow path 47 and the target cell is collected into a reservoir 48 via the flow path 47. FIG. 20 is a cross-sectional view of the flow cell seen from the side. An upstream side of a region 39 has a middle cross section of the flow cell. A downstream side of the region 39 has a cross section along the flow path 47. The flow path 47 is connected to a separated cell reservoir 48. The reservoir is connected to a pulse pump 41 by a sealing system through air. Thus, no solution is discharged to the outside of the flow cell. This method realizes the method described in JP-A No. 2003-302330 on the disposable flow cell. The sample solution, the sheath solution, and the discharged solution, and the collected solution of the separated cells can be all located on the flow cell. This establishes the cell separation method which can cope with biohazard.

A method of performing the cell separation at multiple stages on the flow cell in a different principle will be described with reference to FIG. 21.

This method is intended to separate target particles of a very low density from a high-density contaminating substance particles. Here, a separation method in which a magnetic field is used for a first-stage particle separation, and a pulse flow is used for a second-stage separation will be described.

There is provided a flow cell in which a sample solution containing particles flows. The flow cell has a flow path formed in a transparent substrate and reservoirs formed in the upper portion of the substrate on the upstream side and the downstream side of the flow path, wherein there are a flow path for sample solution introduction connected to the sample reservoir on the upstream side, a flow path 2 for sheath solution introduction connected to the sheath solution reservoir, and a flow path 3 joining these flow paths and narrowing the flow of the sample solution to flow it in laminar flow state. An electromagnet is disposed near the flow path 3 and generates a magnetic field while the sample solution flows. Before being put into the sample solution reservoir of the flow cell, the sample solution is made by mixing magnetic particles with an anti-membrane protein antibody 1 which is a label for a target cell adhering to the surface thereof and at least one fluorescent antibody 2 against another membrane protein which is the label of the target cell. An attraction force attracts the target cell to be separated to a region in which the space density of a magnetic force line is high. By this force, the target particles are shifted from the flow of the sample solution to the flow of the sheath solution. Using this shift, the target cell is separated into a first separation flow path 50 on the downstream side. Separation based on the antibody 1 is performed at this stage. Measurement as to whether or not at least the antibody 2 adheres to the target cell is performed at a measurement region 1. If it is judged that the target cell is a cell in which the antibody 2 is detected, the pulse pump 41 exerts a negative pressure pulse on the target cell through a second separation flow path 52, thereby collecting the target cell into a separated cell collection reservoir 54. Thus, the cell separation accuracy can be improved by combining the different antibody labels with a different separation method.

There will be described a unit configured to improve accuracy in cell separation with magnetic particles using a plurality of antigen-antibody reactions. This method is also intended to separate target particles of a very low density from a contaminating substance particles of high density. The thermo-responsive magnetic nanoparticle of JP-A No. 2007-56094 is a particle in which coagulation and dispersion can be controlled in a solution based on temperature. When the diameter of the magnetic particles is 0.1 micrometers or below, the magnetic moment per particle is reduced and the influence of an external force on the particles by Braunian movement is increased. Thus, a strong gradient magnetic field is necessary for magnetic separation. However, coagulated magnetic particles have a large magnetic moment and can be separated by a weak gradient magnetic field. A thermo-responsive magnetic nanoparticle is comprised of a magnetic particle and a thermo-responsive polymer. A temperature region at the boundary between coagulation and dispersion varies with the properties of the thermo-responsive polymer. Accordingly, the present invention proposes a multi-stage magnetic separation method with multiple magnets. The method includes using particles in which different antibodies are bonded to a plurality of thermo-responsive magnetic nanoparticles in which the coagulation temperature regions are different, and sequentially performs separation utilizing magnetics at different coagulation temperatures. For instance, separation of cells that include both an M antigen and an N antigen from a group of cells that include cells including both the M antigen and the N antigen, cells including either one of them, and cells including neither is performed as follows. With two thermo-responsive magnetic nanoparticles, e.g., an A particle and a B particle, suppose that only the particle A is coagulated at a temperature A and only the B particle is coagulated at a temperature B. The particle A bonded to an M antibody is an M antibody bonded particle A. The particle B bonded to an N antibody is an N antibody bonded particle B. The M antibody particle A and the N antibody particle B are mixed with a cell solution prior to separation so as to allow antigen-antibody reactions. The solution is held at the temperature A and is then exposed to a gradient magnetic field so that the cell bonded to the particle A is separated. That is, cells having the M antigen are separated. Next, the solution containing only separated cells is held at the temperature B and is then separated by a gradient magnetic field so that cells having the N antigen are separated. By the two-stage separation, only the cells having both the M antigen and the N antigen are separated. Next, there will be described a method of identifying whether or not the cell is the target cell with almost no loss of the separated cell solution. The M antibody and the N antibody labeled with fluorescence having different wavelengths are added to the separated cell solution in which magnetic particles are adhered to the cells so as to allow the separated cell to be fluorescently dyed. This sample solution is measured by the flow cytometer. The flow cytometer of the present invention using the flow cell which has reservoirs on the upstream side and the downstream side is used, as shown in FIGS. 1, 2, 3, 7, 16, 17, and 19. This is because the sample solution can be collected without being diluted after measurement. Three branched flow paths on the downstream side and three joining flow paths on the upstream side have the pattern in which they are in substantially symmetrical to each other. Thus, the sample solution and the sheath solution flowing on both sides of the sample solution are separated again and flow into the branched flow paths on the downstream side. The sample solution is not diluted by the sheath solution and is collected into the middle reservoir. The solution containing magnetically separated cells is introduced into the upstream sample reservoir so that the cell solution can be collected on the downstream side without significant loss of the cells after measurement. All the thermo-responsive magnetic nanoparticles used for separation are measured at the temperatures at which they are dispersed. This is because coagulated particles can be clogged in the flow path. Thus, the apparatus may have a mechanism of controlling the temperature of the flow cell. The temperature controlling mechanism heats and cools the components for disposing the flow cell by a Peltier element.

ADVANTAGEOUS EFFECTS OF THE INVENTION

According to the present invention, the flow cytometer or the cell sorter which can replace the entire solution sending system including the sheath solution reservoir together with the flow cell chip is realized. The flow cytometer performing automatic simultaneous parallel measurements of multiple specimens is realized. The cell separation method using a plurality of antigen-antibody reactions is realized.

DESCRIPTION OF THE EMBODIMENTS

There will be described an embodiment of a flow cytometer which can achieve the measurement of a sideward scattered light without losing the function of a disposable flow cell by forming a reflection plane in a flat-plate flow cell.

Figure 1:
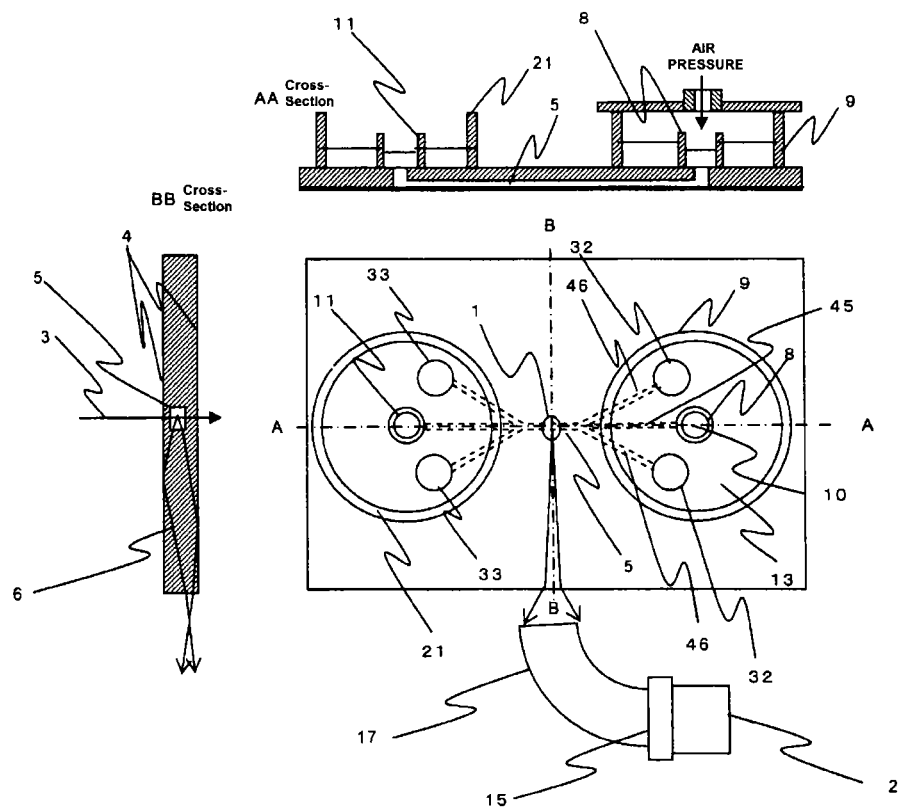
FIG. 1 shows a flow cell chip according to the present invention which has a function to lead a signal light generated in a flow path to an external detector utilizing the front and rear surfaces as reflection planes.

FIG. 1 is a schematic diagram describing the simplest flow cell configuration of the present invention. The material of the flow cell is an acrylic transparent resin. A recessed flow path pattern is formed on the rear surface side of a substrate by injection molding. A sheet having a thickness of about 100 μm is affixed thereonto to form a flow path. The cross section of the flow path typically has a width of 80 micrometers and a depth of 25 to 50 micrometers. The reference numeral 1 denotes an illumination region, which corresponds to the region in which a laser beam as an illumination light illuminates particles flowing through the flow path of the flow cell. A sample solution 10 is filled into a sample solution reservoir 8. The reservoir 8 is connected to a flow path 45 for sample solution. A sheath solution 13 for narrowing and flowing the sample solution is stored in a sheath solution reservoir 9. The reservoir 9 is connected to flow paths 46 for sheath solution. The flow paths 46 for sheath solution join with both sides of the flow path 45 for sample solution so as to flow into one flow path 5. As shown in a cross-sectional view taken along line AA of FIG. 1, the reservoir 9 is higher than the reservoir 8 and the reservoir 9 is pressurized from the outside through the air. The air pressure is applied to the sample solution 10 and the sheath solution 13 at the same time. The pressure value is in the range of 2 to 20 kilopascals. The sample solution and the sheath solution flow towards the downstream side by the pressure and join into the flow path 5. The sample solution is narrowed so as to have a width of about 10 micrometers or below. On the downstream side, three branched flow paths are formed so as to be symmetrical to the joining flow-path pattern on the upstream side. Due to the laminar flow, the sheath solution and the sample solution are separated again and are collected into a discharged solution reservoir 21 and a sample solution collection reservoir 11, which have the same atmospheric pressure as the atmosphere. As the illumination light, a light of a semiconductor laser light source having a wavelength of 473 nm and an output of 10 mW is reduced to have a beam diameter of about 60 micrometers and illuminates the center of the flow path 5 of the region 1 perpendicularly with respect to the substrate of the flow cell from the upper side to the lower side. The instant that particles included in the sample solution passes through the illumination region, a scattered light having the same wavelength as the illumination wavelength and fluorescence having a wavelength longer than the illumination wavelength are generated in pulses. Of these, a signal light 6 generated sideward repeats total reflection on front and rear surfaces 4 of the substrate of the flow cell and reaches an end face at high efficiency. The signal light exiting from the end face to the outside is led to a photodetector by a light guide disposed near the flow cell, and is detected via wavelength selection of a band pass filter 15. The signal is a pulse signal. In addition to the pulse height, the pulse area is recorded for each particle. In the present invention, total reflection in the flow cell is used to detect a sideward signal light. FIG. 1 shows the simplest example for it. In the above example, one detector is used. A plurality of detectors can also be used for a plurality of wavelength separations for the detection of the scattered light and fluorescence. In addition, as a light source, a semiconductor laser having a different wavelength of, e.g., 640 nm can also be used at the same time to illuminate the illumination range so as to detect signals of fluorescence excited by this wavelength separately.

The reason why the light guide is disposed near the flow cell to lead the light to the photodetector is that the flow cytometer has a detection optical system that is hardly affected by a slight position shift when the flow cell is replaced.

Figure 2:
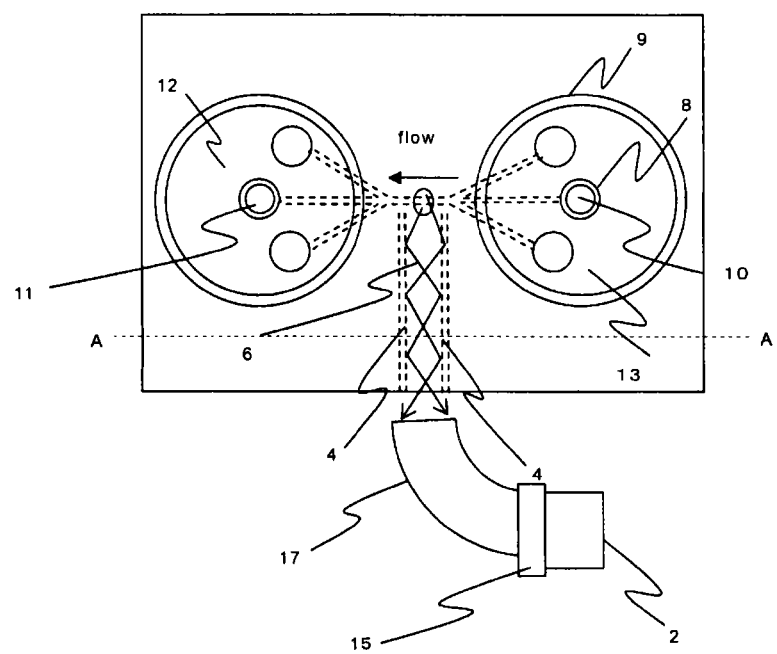
FIG. 2 shows a flow cell chip according to the present invention which has a function to lead a signal light generated in a flow path to the external detector utilizing the front and rear surfaces and the side surface of grooves as reflection planes.
Figure 2:
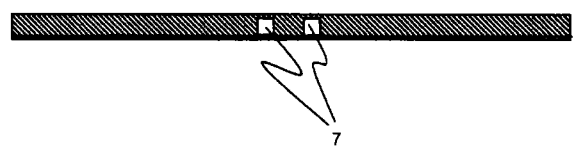

In FIG. 2, a pair of grooves 7 are formed in a substrate of a flow cell. The total reflection plane 4 is formed perpendicularly to the plane of the substrate from near the side surface of the flow path to the end face so that the flow cell has a light guide that functions to limit an enlargement of signal light 6 generated in the flow path in the surface of the substrate, and thereby enhances the detection efficiency of the signal light.

Figure 3:
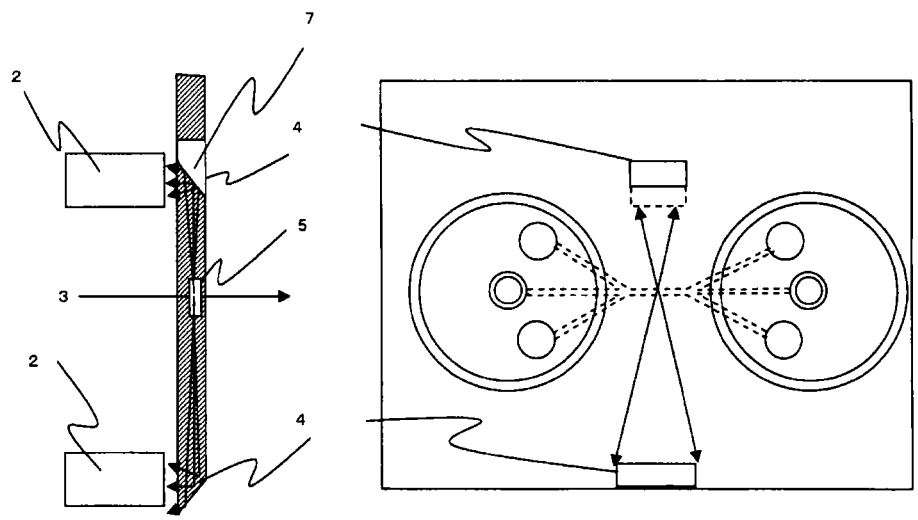
FIG. 3 shows a flat-plate flow cell according to the present invention which has a function to reflect a signal light generated in the flow path in the direction perpendicular to the plane of the flow cell and lead it to the external detector utilizing the reflection plane formed near the side surface of the flow path.

FIG. 3 shows a method of detecting a sideward signal light generated from a flow path by detectors disposed on a surface, not in the end face direction, using a total reflection plane formed in a flow cell. This drawing shows an example in which the signal light is reflected on the surface, which is ditto for the rear surface direction. This drawing shows a position of the total reflection plane in the substrate and a position of the total reflection plane at the end edge of the substrate. The total reflection planes in both positions are formed at the boundary between the resin and the atmosphere. When being formed in the substrate, the total reflection plane can be formed near the side surface of the flow path. There is a merit that the sideward signal light can be detected before being enlarged. The total reflection plane formed by an inclined surface on the end face has a demerit that it is far away from the flow path, but a great merit that the quality control for manufacture of inclined surface formation is easy.

Figure 4:
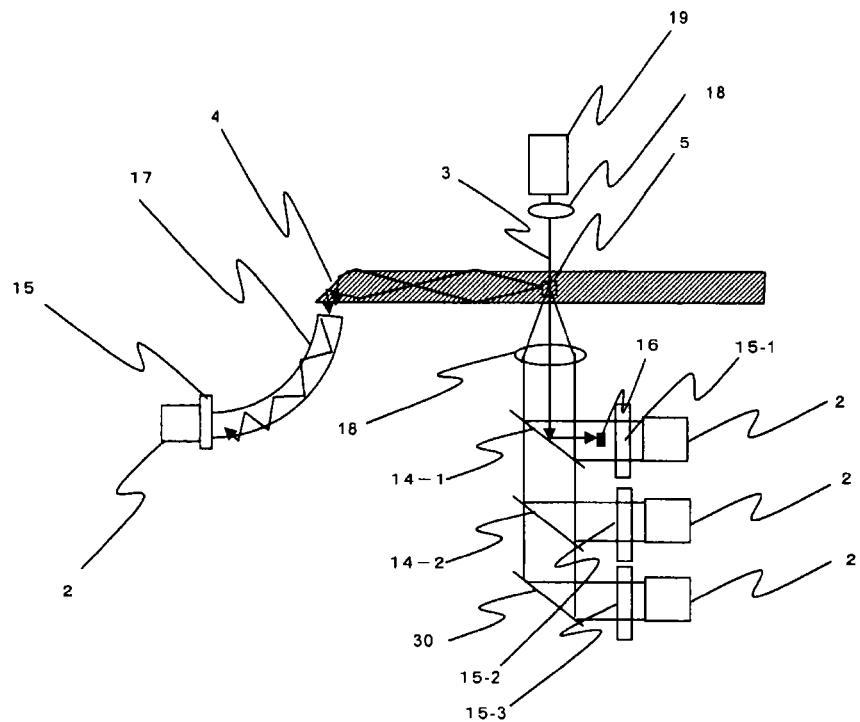
FIG. 4 shows an optical system of an apparatus performing simultaneous detection of a sideward scattered light and a forward scattered light by a flow cell chip incorporating reflection according to the present invention.
Figure 7:
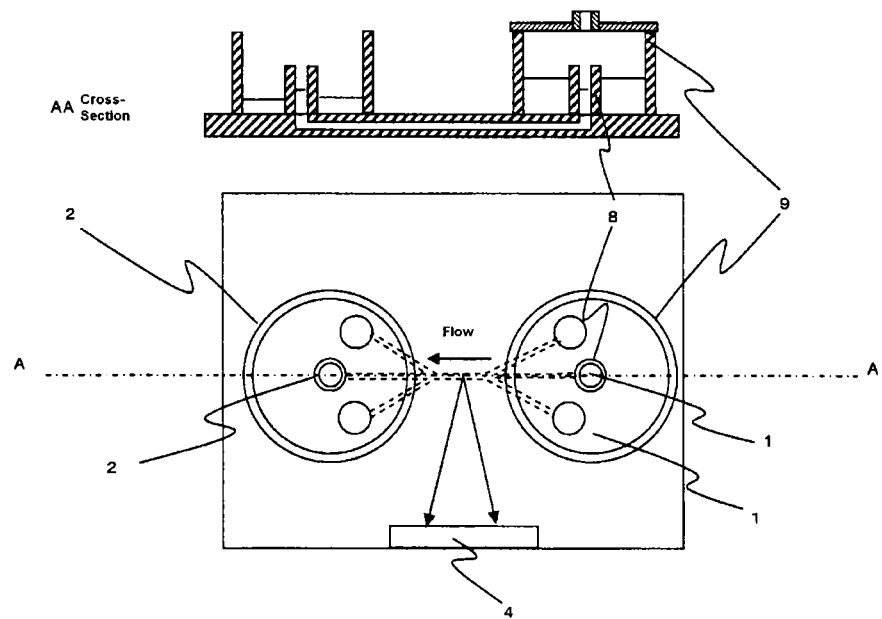
FIG. 7 shows a configuration of a flow cell chip incorporating reservoirs and two reflection planes according to the present invention.

FIG. 4 shows an example of an optical system which can detect, as signal lights, the sideward scattered light and fluorescence as well as the forward scattered light by the flat-plate flow cell. A semiconductor laser having a wavelength of 473 nm is used as a light source. The sideward scattered light is detected using the total reflection plane of the end face of the flow cell via the light guide and the band pass filter passing the illumination light having a wavelength of 473 nm. In the detection of the forward scattered light, the signal light passing through the bottom surface of the flow cell is collimated by a lens, the collimated light is reflected by a dichroic mirror 14-1 reflecting the light of 473 nm and passing the light having a longer wavelength, the direct transmission light of the illumination light is cut by a shielding plate 16, and the forward scattered light is detected by the photodetector such as a photo diode via a band pass filter passing only the illumination light having a wavelength of 473 nm. As in the forward scattered light, a fluorescence detection wavelength is selected from the signal light passing through the bottom surface of the flow cell and passing through the dichroic mirror 14-1 by a combination of a dichroic mirror 14-2 and a band pass filter 15-2 or a band pass filter 15-3 for a detection optical system on the most downstream side, and fluorescence is detected by a photomultiplier tube. As for the selection of the fluorescence detection wavelength, when FITC is used as the fluorescent reagent, a fluorescence detection wavelength of 510 to 550 nm is preferable, when PI is used as the fluorescent reagent, a fluorescence detection wavelength of 570 to 620 nm is preferable, when Cy5 is used as the fluorescent reagent, the fluorescence detection wavelength of 660 to 720 nm is preferable, and when Cy7 is used as the fluorescence reagent, the fluorescence detection wavelength of 750 to 800 nm is preferable. FIG. 7 is a schematic top view of the flow cell shown in FIG. 4. A reflection plane 4 is formed on the end face of the substrate. The flow rate of the sample solution is controlled by the atmospheric pressure in reservoir 9 on the upstream side.

Figure 5:
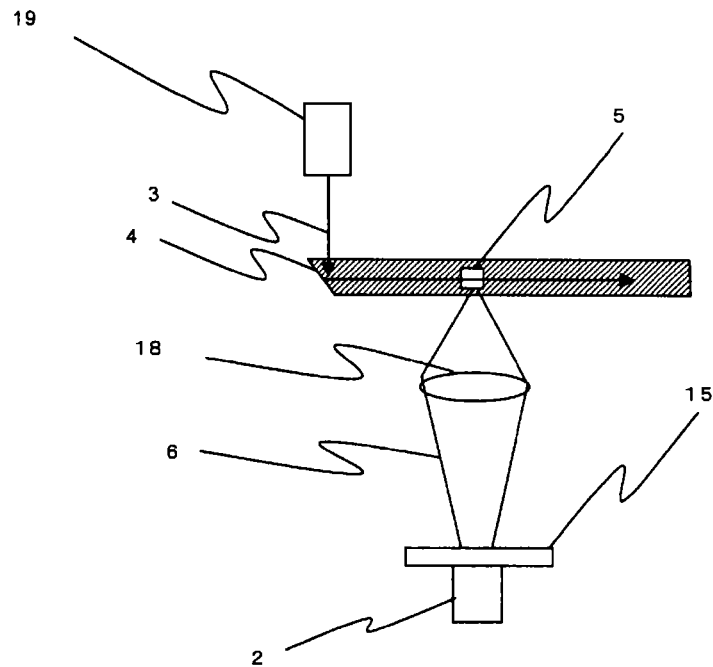
FIG. 5 shows an optical system using a reflection plane in a chip for reflection of an illumination light according to the present invention.

In FIG. 5, the illumination light that enters at the total reflection plane formed in the substrate of the flow cell is used to illuminate the flow path 5 in an in-plane direction of the flow cell. The light passing through the bottom surface of the flow cell becomes the sideward signal light.

However, this has a greater merit when applied to the flow cell for multiple specimens as described later.

Figure 6:
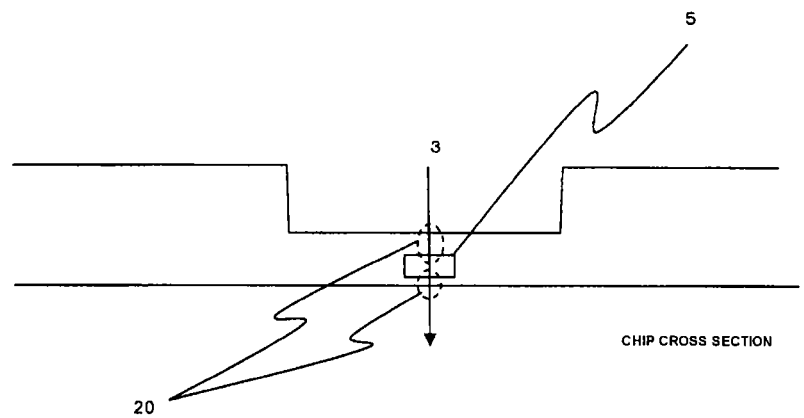
FIG. 6 shows a configuration reducing fluoresce generated from the flow cell itself.

FIG. 6 shows a method of reducing fluorescence generated from a resin flow cell itself. Slight light absorption at 400 nm or above exists in a transparent acryl resin. Illumination of the resin with an intense laser beam having a wavelength of 473 nm generates fluorescence over an entire illuminated region of the acryl. To reduce the fluorescence intensity, the illumination region through which the laser passes is made thinner than the periphery thereof. This method overcomes two disadvantages that the thinning of the entire periphery easily deforms the flow cell and the thickening of the entire periphery increases the fluorescence intensity from the flow cell. This technique is combined with the technique of forming a total reflection plane in a flow cell to detect a sideward signal light, whereby a background noise light in a detection of the sideward signal light, and in a detection of fluorescence in particular, can be reduced.

An embodiment of a flow cytometer for multiple specimens will be described.

Figure 8:
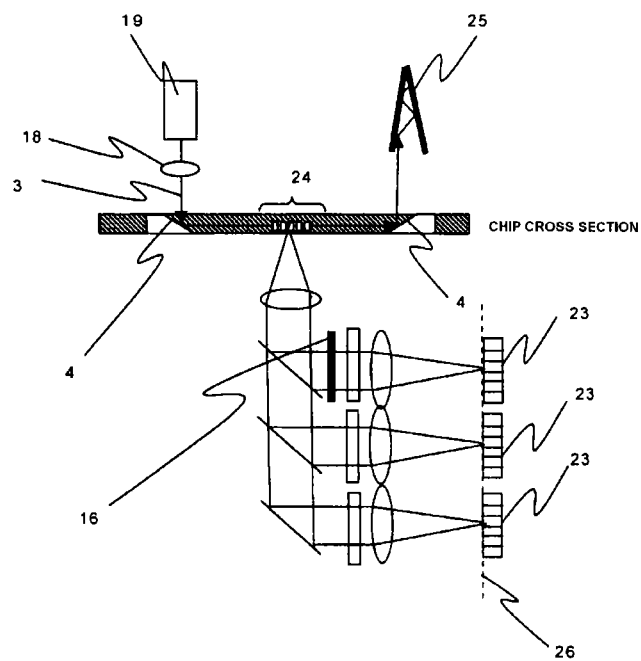
FIG. 8 shows a method including reflecting a light on reflection planes formed in a chip and illuminating the side surfaces of multiple flow paths at the same time according to the present invention.
Figure 9:
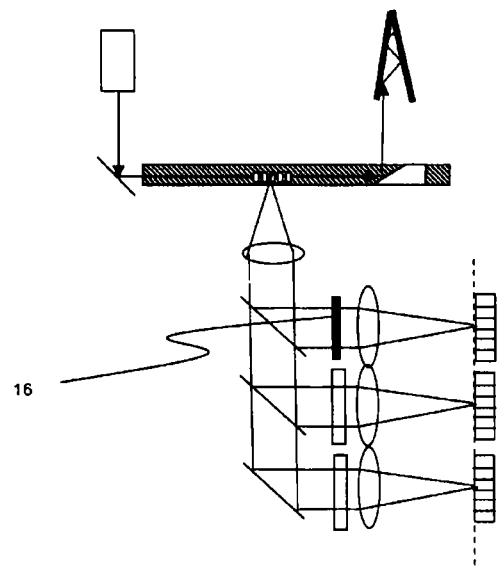
FIG. 9 shows a method of illuminating the side surfaces of multiple flow paths at the same time using the reflection plane disposed outside the chip according to the present invention.
Figure 10:
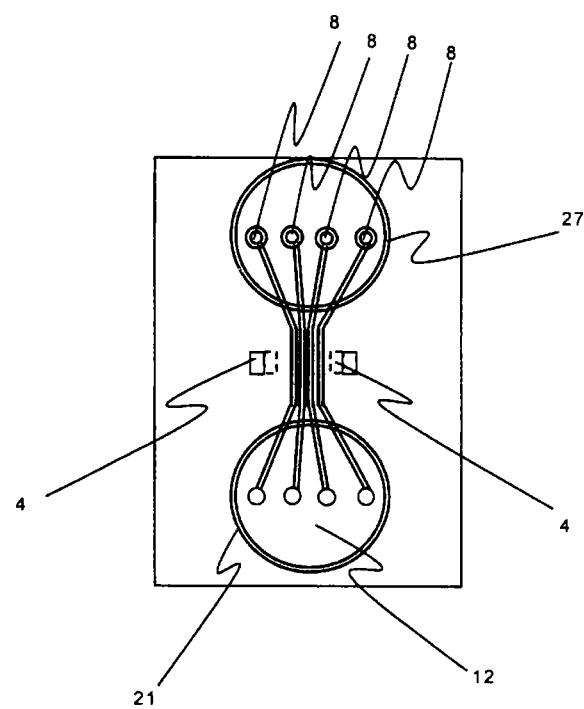
FIG. 10 shows a plan view of the flow cell according to the present invention shown in FIG. 8.

An embodiment shown in FIG. 8 is a method of illuminating flow path 5 in an in-plane direction of the flow cell substrate using an illumination light from a total reflection plane formed in the substrate of the flow cell, as in FIG. 5. A plurality of flow paths are formed in the flow cell. FIG. 10 is a top view of the flow cell. In this case, no solution is put into an upstream side reservoir 27 which is instead used as a pressurized space for applying a common air pressure to the plurality of sample solution reservoirs 8. The flow paths, each of which is connected to respective one of plurality of sample solution reservoirs 8, are formed in the substrate in an array at equally spaced intervals. The width of the flow path is 80 micrometers and the pitch between the flow paths is also 80 micrometers. The illumination laser illuminates the flow paths so as to penetrate therethrough. The direct transmission light of the illumination light is reflected at the other total reflection plane in the direction perpendicular to the surface of the substrate, and is absorbed to the light absorption member. If there is no reflection plane, the transmission light of the illumination light illuminates the end face to generate scattered light which becomes strong noise. The reason why the direct transmission light of the illumination light is absorbed to the light absorption member is that returning of the light to the flow path affects the detection signal waveform. As shown in FIG. 8, to distinctively detect each of the flow paths, the detection optical system has an array photodetector which is arranged on an image formation plane of the flow path. In FIG. 9, an external mirror is used without utilizing the total reflection in the flow cell.

The flow paths are parallel with each other. The diffraction light generated from the interface of the flow path is linearly focused and is easily removed by the band-shaped space filter 16. This is a method of preventing deterioration of detection sensitivity of the scattered light signal.

Figure 11:
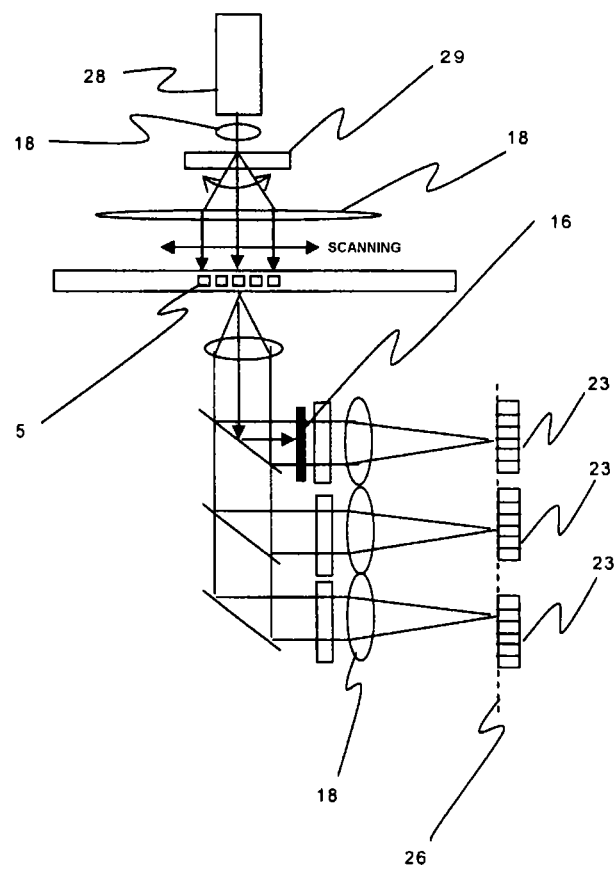
FIG. 11 shows a method including scanning multiple flow paths with a laser beam at high speed using a deflector, illuminating the flow paths at the same time, and measuring each of the flow paths according to the present invention.

An embodiment shown in FIG. 11 represents a method of measuring a plurality of sample solutions flowing through a plurality of flow paths at one time by scanning the illumination laser light at high speed. The laser light source collimates the semiconductor laser having a wavelength of 473 nm by a size of a diameter of 1 mm, and scans the orientation of the laser light at high speed using a deflector 29 with an A0 modulation element. A later-stage lens 18 of the deflector collimates the beam whose orientation has been changed, and converts the scans of the change in orientation angle to scans in parallel movement. The scanning frequency of the deflector is about 40 MHz. The response frequency of the signal processing system of the photodetector is set to about 20 kHz so that the scanning is faster 1000 times or more. The illumination system is identified by the detection system by a line beam extended to the scanning width. It is important that the flow paths be parallel with each other. This is because although the diffraction light from a wall surface of the flow path is distributed in the direction perpendicular to the wall surface of the flow path, the wall surfaces of the flow paths are parallel so that each of the diffraction lights is linearly distributed and can be removed by a narrower band-shaped light shielding plate. The light shielding plate is space filter 16 used for cutting the transmission light of the illumination light in the forward scattered light detection optical system.

In the detection optical system, an array detector 23 is disposed, as the image formation optical system for distinguishing and detecting the flow paths, on an image formation plane 26 of the flow path. The flow cell of FIG. 11 does not require the sheath flow and is the same as FIGS. 8 and 10.

Figure 12:
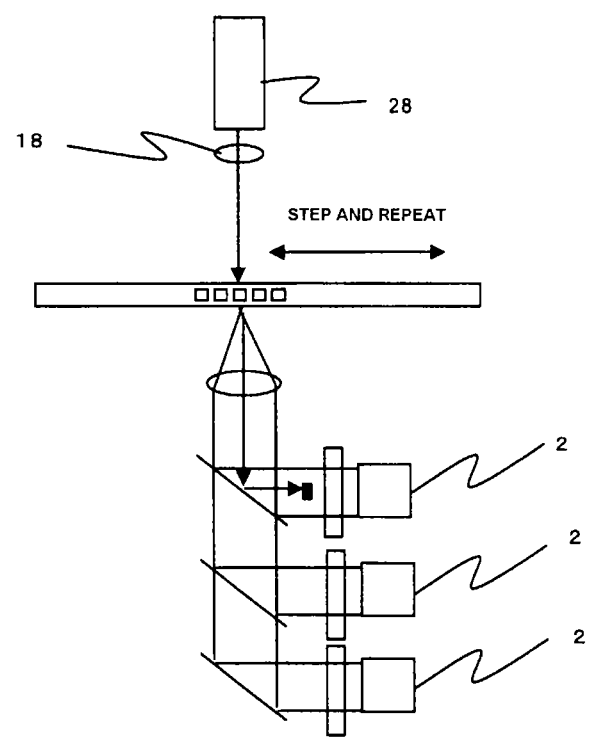
FIG. 12 shows a method including sequentially moving a flow cell chip by step and repeat and sequentially measuring with multiple flow paths according to the present invention.

The embodiment shown in FIG. 12 represents a method of sequentially measuring a plurality of flow paths, not a method of simultaneously measuring a plurality of flow paths in parallel. In this case, although the measurement time is longer than the simultaneous parallel measurement, the detection optical system need not distinguish the flow paths. Thus, as in FIG. 1, the image formation optical system and the array detector are unnecessary. As for the method of sequentially measuring the flow paths, both the method of moving the flow cell by step and repeat and the system of the scanning with the illumination laser light by step and repeat are applicable.

Figure 13:
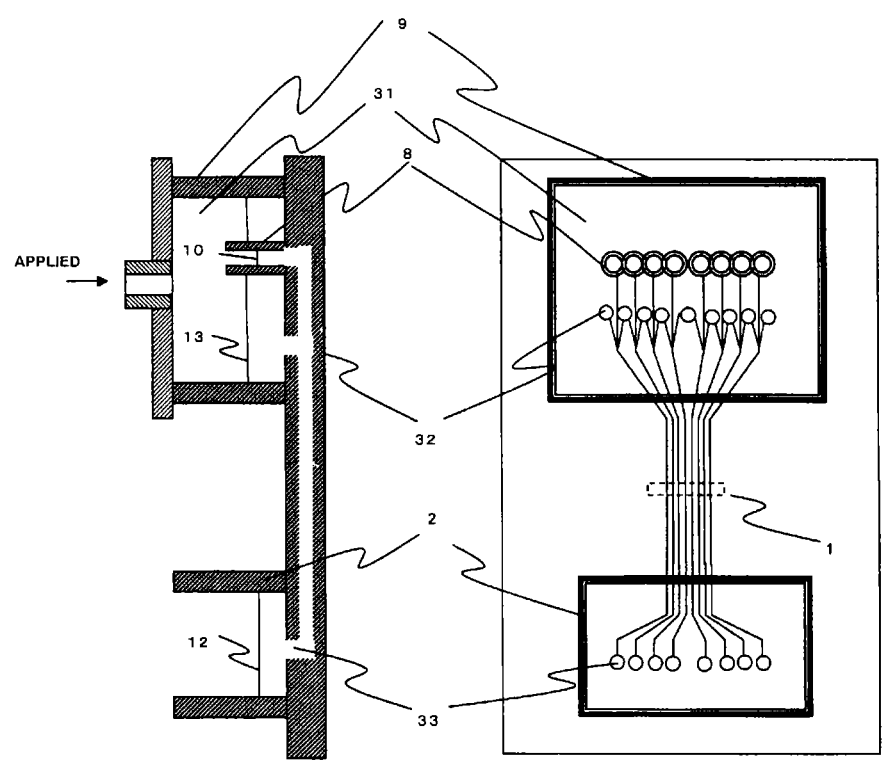
FIG. 13 shows a flow cell for multiple specimens according to the present invention in which a plurality of sample solution reservoirs, a common sheath solution reservoir, and multiple flow paths are formed.

FIG. 13 shows a flow cell configuration suitable for the step and repeat system. As in FIG. 1, the illumination laser beam has a beam size for measuring only one flow path. Thus, the width of a sample solution flow in all of the plurality of flow paths is limited to 10 micrometers or below by the sheath flow. The region in which the laser light is moved is the region 1. Because it adopts a step and repeat system, all the flow paths have a width of 80 micrometers and a uniform pitch of 80 micrometers. All of the sample flows are supplied from the common sheath solution reservoir 9 via a pair of sheath solution introduction ports 32 corresponding to each of the sample solution flows. The plurality of sample solutions flow altogether by application of pressure with the reservoir 9. In order that the measurement of each of the samples is completed before the sample solution is lost from the sample solution reservoir, the sample flow rate and the measurement time are adjusted by the pressure. In the case of a flow path having a flow path width of 80 micrometers and a depth of 25 micrometers, the sample solution of 100 microliters continue to flow for 30 minutes or more under pressuring conditions where the air pressure of the reservoir 9 is 20 kilopascals. Eight sample solution reservoirs are used. The measurement time per sample is one minute. The movement time between the flow paths is two seconds. Thus, the measurements of the eight samples are completed within ten minutes. The discharged solution is stored into the discharged solution reservoir 21 via a collecting port 33 connected to each of the flow paths. The discharged solution reservoir 21 has the atmospheric pressure.

Figure 14:
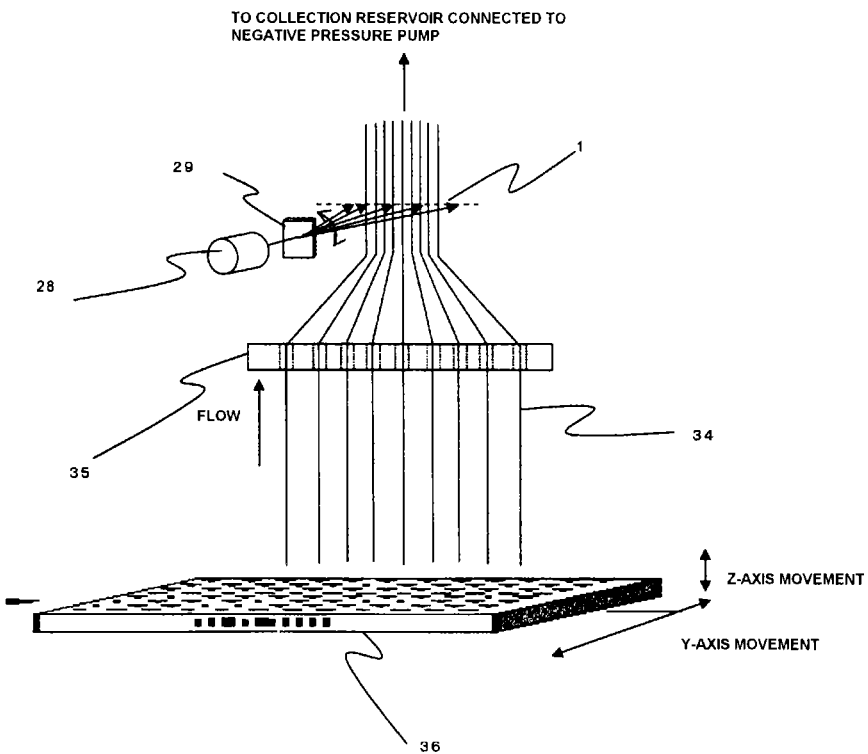
FIG. 14 shows a method adopted for multiple specimens by scanning a flow cell as a capillary array with a laser beam according to the present invention.
Figure 15:
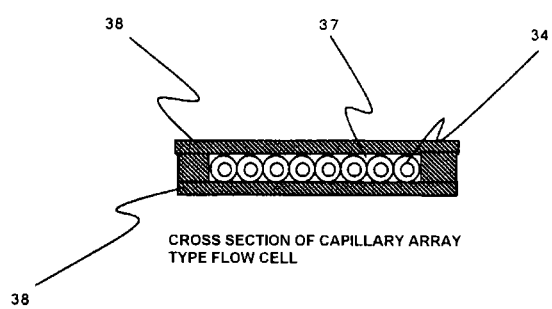
FIG. 15 shows a cross sectional view of the flow cell of the capillary array of FIG. 14.

FIG. 14 does not represent an embodiment of the flow cytometer in which the entire solution sending system is formed on the flow cell. However, it represents an embodiment performing automatic measurements of multiple specimens to cope with disadvantages when the disposable flow cell is used, and represents a method using the laser beam high-speed scanning of the present invention, which is described as an embodiment of the present invention. Here, the flow cell has micro-capillaries fixed in an array and is scanned with the illumination laser beam having a length larger than the width of the capillary array at high speed. As in FIG. 11, to distinguish the capillaries, an image formation optical system and an array detector are used for the laser light source and the detection optical system. The capillary is made of quartz and has an inner diameter of 75 micrometers and an outer diameter of 150 micrometers. As shown in FIG. 15, the flow cell is made in such a manner that the gaps between the eight capillaries are filled with a refractive index matching solution having a refractive index of 1.42 and the capillaries are sandwiched between two quartz plates and fixed. In this way, the intensities of the reflection light and the diffraction light generated when the laser beam illuminates the surface of the capillary are reduced. For the pretreatment of multiple specimens, a 96-well plate, for instance, is used. The wells into which the samples are put are arrayed in a 8×12 matrix. The eight capillaries are matched to the pitch of the eight rows of the 96-well plate by an adjusting jig 35. For the measurements of one row, an up-and-down movement of the plate, movement along the column, and sample solution suction measurement are repeated 12 times to complete the measurement of 96 samples.

An embodiment of a cell separation apparatus using a disposable flow cell will be described.

Figure 16:
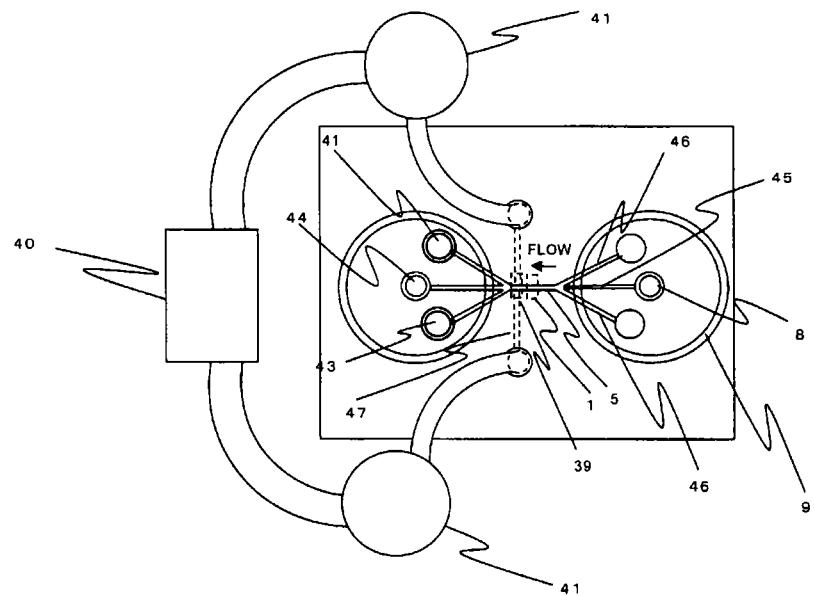
FIG. 16 shows a first example of the flow cell for particle separation according to the present invention.
Figure 17:
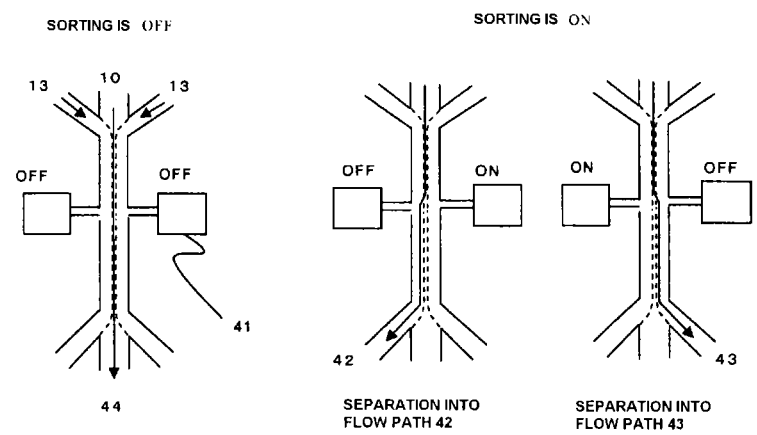
FIG. 17 shows a particle separation method using the flow cell chip of FIG. 16.
Figure 18:
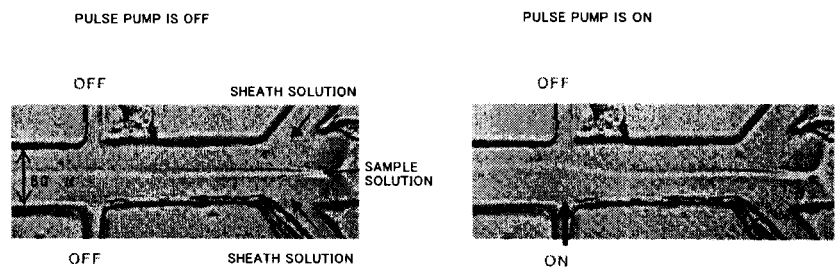
FIG. 18 shows a photograph of the states of FIG. 17 observed in the micro-flow path.

FIG. 16 shows a first example of a flow cell for particle separation of the present invention. As in the flow cell described in FIG. 1, the material of the flow cell is a transparent acryl resin, a recessed flow path pattern is formed on the rear surface side of a substrate by injection molding, and a sheet having a thickness of about 100 μm is affixed thereonto to form a flow path. The configuration of the flow cell of FIG. 16 is based on the configuration of FIG. 1, and has a flow path pattern in which sorting flow paths 47 are connected to the flow path 5 from both sides. A pulse pump 41 of the outside of the flow cell is connected via a pipe to each of the flow paths 47. The flow path 5 has a flow path width of 80 micrometers and a depth of 25 micrometers. The flow path 47 also has a flow path depth of 25 micrometers, but a flow path width of 25 micrometers which is the same as the depth. This is because the ratio of the groove width and the depth of the processing of the die for injection molding is 1, which is the current practical processing limit. When the depth of the flow path is 50 micrometers, the width of the flow path 47 is required to be 50 micrometers. The pulse pump is operated by the extension and contraction motion of the piezoelectric device. The piezoelectric pump has the performance of time responsive properties up to 100 Hz and a pulse pressure of about 0.9 M pascals. The flow volume is adjusted to be 0.5 nanoliters per pulse. The spatial resolution of the cell separation by one pulse is determined by the value obtained by dividing the flow volume of one pulse by the sectional area of the flow path and the flow rate. When the flow path width is 80 micrometers, the depth is 50 micrometers, and the speed is 200 millimeters/sec, the spatial resolution is 125 micrometers. The piezoelectric device is strong against compression stress but is easily broken with respect to tension stress. Only the shift by the force generated in the extension direction by the application of the compression stress can be used. One piezoelectric pump is required to correspond to an occurrence of a pulse flow in one direction. The pulse flow in the pushing-out direction is used, and for this reason the supplied solution tank for sorting is connected to the piezoelectric pump. A PBS buffer solution is held in the tank. It is required that there is no damage to a cell flowing through the flow path 5 when it is mixed with the pulse flow. The timing at which the pulse flow of the piezoelectric pump is generated can be set by the delay time from the detection of the signals of the scattered light and fluorescence generated when a particle passes through the measurement region 1. The delay time is the time by which a particle reaches from the detection region 1 to separation region 39. The delay time is set depending on the speed of the particle. It is judged in real time based on the distribution of the signal intensities of the scattered light and fluorescence whether or not the particle is the target particle. If the particle is the target particle, only the piezoelectric pump corresponding to one of two target cells is turned on. In this process, based on the result of the signal processing of the signal light, a trigger signal is fed to a piezoelectric pump driver circuit of the corresponding piezoelectric pump after a fixed delay time from the signal detection. The driver circuit inputs a voltage signal for one pulse to the piezoelectric pump to turn on the pulse pump. The position in which the target particles receive the pulse flow and flows is shifted. As shown in FIG. 17, of the three branched flow paths on the downstream side, a middle branched flow path 44 is the flow path into which the particles flow when the pulse pump is in the OFF state. When the pulse pump is in the ON state, the particles flow into a branched flow path 42 by the shift of the pulse flow. FIG. 18 shows a photograph of an observed instant that a flow is shifted by a pulse flow. The flow line of the sample solution is made visible by putting an ink into only the sample solution. While the piezoelectric pump is off, the sample solution surrounded by the sheath solution flows through the middle portion of the flow path. When the pulse flow is applied from the side surface of the flow path on the downstream side, it can be seen that the flow of the sample solution is shifted.

Figure 19:
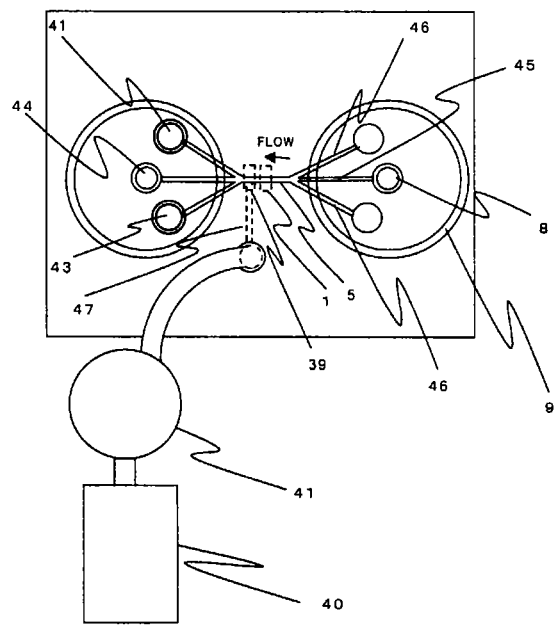
FIG. 19 shows an example in which one pump is used in the particle separation method of FIG. 16.

The two target particles are separated by the flow cell in which the two sorting flow paths 47 are connected to the flow path 5 so as to be opposite. As shown in FIG. 19, only one flow path 47 is used so that one target particle can be separated.

Figure 20:
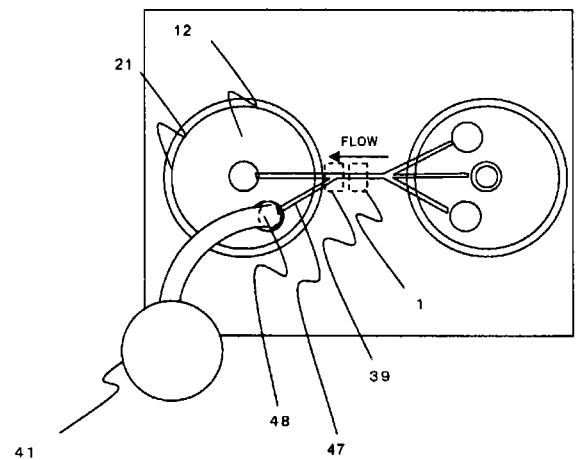
FIG. 20 shows a second example of the flow cell for particle separation according to the present invention.
Figure 21:
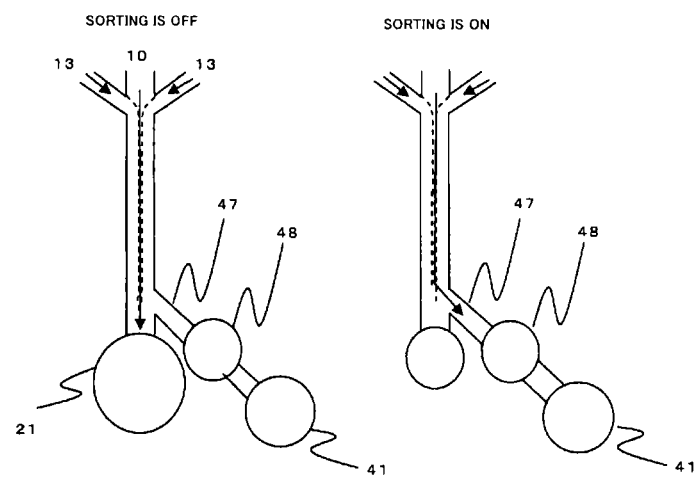
FIG. 21 shows a particle separation method using the flow cell of FIG. 20.
Figure 22:
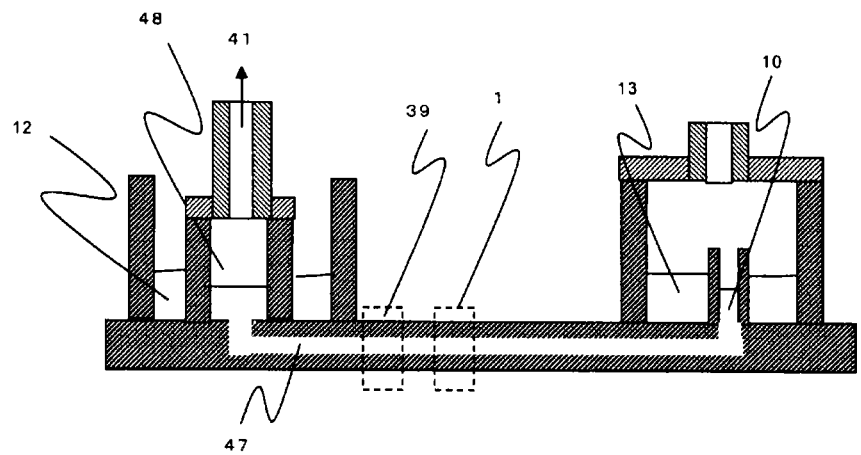
FIG. 22 is a cross-sectional view of the flow cell of FIG. (31) 20.

An example in which a shift of a flow of target particles by a pulse flow is not used but the target particles are fetched by the pulse flow itself will be described with reference to FIG. 20. In the flow cell of FIG. 20, the instant that the particles identified as the particles to be separated in the measurement region 1 passes through the particle separation region 39, the pulse flow drawn into the flow path 47 is fetched by the pulse pump connected to the flow path 47 and the separated particles are stored in a separated-particle reservoir 48. The state of the separation is shown in FIG. 21. FIG. 22 is a cross-sectional view of the flow cell configuration. The separated particle reservoir 48 and the pulse pump are connected via the air. The separated particles are stored in the separated particle reservoir 48. When the pulse flow is operated above the volume of the separated particle reservoir, the separated particle solution flows into the pulse pump. To prevent this, the number of pulses of the separation process for one sample is limited. The flow volume per pulse of the pulse pump used is about 0.5 nanoliters. The separated particle reservoir has a volume of 200 microliters. Thus, the maximum number of pulses for separation is limited to 400000 times or below. By this, the cells to be separated are not leaked to the outside of the flow cell and the cell separation apparatus copes with biohazard. FIG. 20 is a diagram in which only one pulse pump is disposed. As in FIG. 16, three branched flow paths on the downstream side are used to dispose the pulse pumps on both sides of the reservoir, thereby enabling the separation of two kinds of particles. The process from the signal processing to the operation of the pulse pump is the same as the embodiment of FIG. 16.

Figure 23:
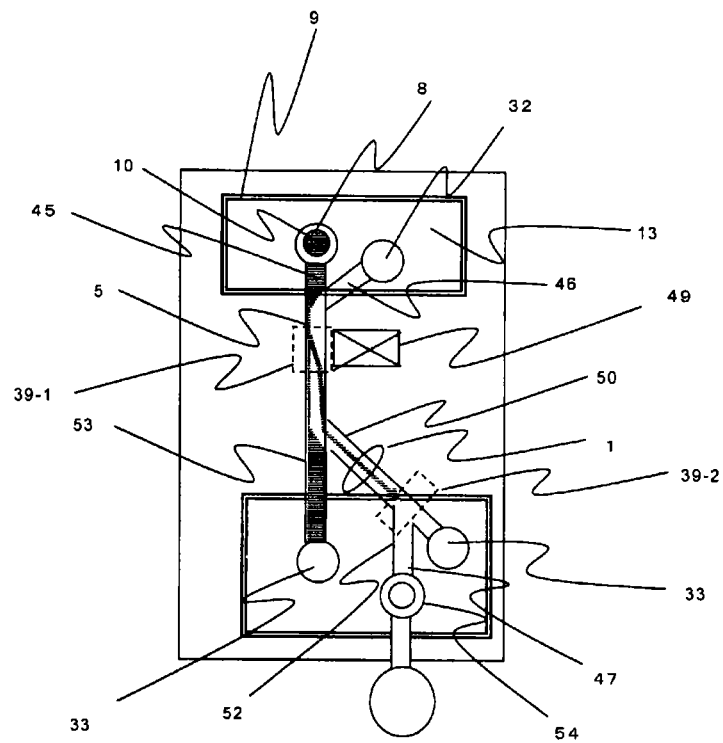
FIG. 23 shows an example of a flow cell chip for particle separation at multiple stages according to the present invention.

An embodiment of a method for performing cell separation on the flow cell at multiple stages according to a different principle will be described. FIG. 23 schematically shows a configuration in which separation using a magnetic field is performed at a first stage and separation using the pulse flow is performed in one flow cell at a later stage. A sample solution is a solution made by mixing a specimen including various cells with magnetic particles coated with an antibody bindable to a membrane protein of a target cell for separation, a fluorescence antibody bindable to another membrane protein of the target cell (the fluorescence reagent is Cy5 and the like), and a nucleus dye (such as SYTO9) for distinguishing between a cell and a biomembrane fragment. As in the flow cell of FIG. 1, sample solution reservoir 8 is formed within sheath solution reservoir 9 on the upstream side. However, one flow path for sheath solution 46 is sufficient in this embodiment. This is because the sample solution 10 should flow so as to concentrate on the end of the flow path 5, and unlike FIG. 1, is not required to concentrate on the center portion. In the particle separation region 39-1, magnetic particles having a magnetic moment are drawn to a region in which the density of magnetic force lines is high by the magnetic force generated by a magnet. The strength of the magnetic field is adjusted by an electric current of the electromagnet. In order that the speed of the migration of the magnetic particles by the magnetic field can obtain a sufficient amount of shift while the particles pass through the particle separation region 39-1, the flow rate of the sample is adjusted by a pressure. As to the relation between a first separation flow path 50 and a flow path for discharged solution 53, a flow path is formed so as to be in substantially symmetrical to the flow path 45 and the flow path 46 on the upstream side. The sheath solution flows so as to be separated into the flow path 50 on the downstream side. When the flow of the magnetic particles flow towards the sheath solution by the magnetic field, it flows to the first separation flow path 50. The particle measurement region 1 illuminated with a laser is located within the flow path 50. As the laser light source, two semiconductor lasers having a wavelength of 473 nm and 640 nm are used. The laser beam of 473 nm is used for exciting SYTO9 and the laser beam of 640 nm is used for exciting Cy5. The two laser beams having a beam size of 160 micrometers larger than the flow path width of 80 micrometers of the flow path 50 uniformly illuminate the flow path 50. The particles emitting fluorescence of a fluorescence antibody and the fluorescence of a nucleus dye in this region is separated by a dichroic mirror and a band pass filter based on the wavelength for detection, as in the detection optical system shown in FIG. 4. In a second separation flow path 52 on the downstream thereof, the particles are stored in a separated cell reservoir 54 by the pulse flow drawn from the flow path 47 connected thereto. The pulse pump is connected to the reservoir 54 via the air and the separated cell fluid cannot flow out to the pump side. This solution is the same as the biohazard solution described in FIG. 22. Thus, a magnetic separation and a separation using a pulse flow by a fluorescence signal are realized on a flow cell.

Next, an embodiment of magnet separation at multiple stages by a plurality of thermo-responsive magnetic nanoparticles will be described. Three thermo-responsive magnetic particles of Therma-MAX LSA Streptavidin, Therma-MAX UB Biotin, and Therma-MAX LB Biotin manufactured by Magnabeat Incorporated are used. These particles have an average particle diameter of about 100 nm. Therma-MAX LSA Streptavidin is a thermo-responsive magnetic particle which has properties in which it is coagulated at 30° C. or above and is dispersed at 20° C. or below, has a surface bonded to streptavidin, and can be coated with various antibodies bonded to biodin. Therma-MAX UB Biotin is a thermo-responsive magnetic particle which has properties in which it is dispersed at 10° C. or above and is coagulated at 4° C. or below, has a surface bonded to biotin, and can be coated with various antibodies bonded to avidin. Therma-MAX LB Biotin is a thermo-responsive magnetic particle which has properties in which it is dispersed at 32° C. or below and is coagulated at 42° C. or above, has a surface bonded to biotin, and can be coated with various antibodies bonded to avidin.

Three antibodies of a monoclonal antibody (anti-EpiCAM) to a surface antigen (EpiCAM) specifically expressed on an epithelial cell, a monoclonal antibody (anti-CK) to a cytokeratin, and a monoclonal antibody (anti-CD45) to CD45 are bonded to the above-mentioned three kinds of particles, respectively. These magnetic particles will be referred to as an anti-EpiCAM particle, an anti-CK particle, and an anti-CD45 particle, respectively. The three kinds of particles are mixed with a blood specimen of 10 mL or below to cause three antigen-antibody reactions. A magnet is brought close to the solution at 42° C. at which the anti-CD45 particle is coagulated to exert the gradient magnetic field, thereby removing the cell absorbed to the anti-CD45 particle together with the particles from the blood specimen. A magnet is then brought close to the remaining solution at 30° C. at which the anti-EpiCAM particle is coagulated to exert a gradient magnetic field, and then, the cell absorbed to the anti-EpiCAM particle and the particle itself are collected so as to be suspended in a PBS buffer solution. A magnet is brought close to the solution at 4° C. to exert a gradient magnetic field, and then, the cell absorbed to the anti-CK particle is collected so as to be finally suspended in the PBS buffer solution of 100 μL. The final suspension includes the anti-EpiCAM particle and the anti-CK particle. While the final suspension is held at 20° C. at which both are dispersed, the final suspension is measured by the flow cytometer exemplified by the present invention using the flow cell capable of collecting the sample solution. The total number of cells is measured. The measured cells are collected. According to Japanese Patent Application Laid-Open (JP-A) No. 2007-178193, this cell is a suspended cell included in blood and corresponds to a cancer cell circulated in blood as a cause of metastasis.

EXPLANATION OF REFERENCE NUMERALS

1 . . . Illumination region (measurement region)
2 . . . Photodetector
3 . . . Illumination light
4 . . . Light reflection plane
5 . . . Flow path
6 . . . Signal light (scattered light or fluorescence)
7 . . . Gas
8 . . . Sample solution reservoir
9 . . . Sheath solution reservoir
10 . . . Sample solution
11 . . . Collected sample solution
12 . . . Discharged solution
13 . . . Sheath solution
14 . . . Dichroic mirror 15 ... Band pass filter
16 ... Space filter
17 ... Light guide
18 ... Lens
19 ... Illumination light source
20 ... Fluorescence generation region from the basic material of a chip
21 ... Discharged solution reservoir
22 ... Sample solution collection reservoir
23 ... Array type photodetector
24 ... Region formed with a plurality of flow paths
25 ... Light absorption portion
26 ... Image formation plane
27 ... Gas pressurization reservoir
28 ... Laser light source
29 ... Deflector
30 ... Mirror
31 ... Pressurized space
32 ... Sheath solution introduction port
33 ... Collection port
34 ... Capillary
35 ... Interval adjusting instrument
36 ... Multi-well plate sample case
37 ... Refractive index matching solution
38 ... Quartz plate
39 ... Particle separation region
40 ... Supplied solution tank for sorting
41 ... Pulse pump
42 ... Reservoir A
43 ... Reservoir B
44 ... Reservoir C
45 ... Flow path for sample solution
46 ... Flow path for sheath solution
47 ... Flow path for pulse flow
48 ... Separated cell fluid
49 ... Electromagnet
50 ... First separation flow path
52 ... Second separation flow path
53 ... Flow path for discharged solution
54 ... Separated cell reservoir

The invention claimed is:

1. An apparatus for analyzing particles in a solution comprising:
a flow cell having a flow path for flowing a sample solution containing the particles;
a unit configured to illuminate the sample solution flowing through the flow path of the flow cell;
photodetectors that detect, based on the wavelength, scattered lights and/or fluorescence generated from each particle in the sample solution; and
a unit configured to individually analyze the particles based on their signal intensities detected by the photodetectors;
wherein the flow cell has the flow path formed in a substrate, a reflection plane is formed on the outer side surface of the flow path, the reflection plane directs the sideward scattered light which is generated in the flow path of the flow cell to a specified region of the surface of the flow cell, and the photodetectors detect the light exiting from the specified region to the outside.

2. The apparatus for analyzing particles in a solution according to claim 1, wherein the reflection plane formed on the outer side surface of the flow path side is a plane formed from the interface between the side surface of the flow path and an atmospheric gas, and is a plane that totally reflects the light arriving from the flow path.

3. The apparatus for analyzing particles in a solution according to claim 1,
wherein the flow cell is a flat-plate flow cell, the apparatus has a configuration that allows an illumination light to enter into the flow path substantially perpendicularly to the surface of the substrate of the flat-plate flow cell, the sideward scattered light generated in the flow path is detected as the light which is directed from the specified region of the surface of the flow cell sideward by means of the reflection plane in the substrate of the flow cell, and a forward scattered light generated in the flow path is detected as the light which passes through the flow cell and reaches outside the substrate of the flat-plate flow cell.

* * * * *